United States Patent [19]

Ostreicher et al.

[11] Patent Number: 4,708,803

[45] Date of Patent: * Nov. 24, 1987

[54] LIQUID FILTRATION USING HYDROPHILIC CATIONIC ISOTROPIC MICROPOROUS NYLON MEMBRANE

[75] Inventors: Eugene A. Ostreicher, Farmington; Rodney A. Knight, New Milford; Joseph V. Fiore, Fairfield; George T. Emond, Southington, all of Conn.; Kenneth C. Hou, San Antonio, Tex.

[73] Assignee: Cuno Incorporated, Meriden, Conn.

[ * ] Notice: The portion of the term of this patent subsequent to Sep. 25, 2001 has been disclaimed.

[21] Appl. No.: 648,401

[22] Filed: Sep. 6, 1984

Related U.S. Application Data

[63] Continuation of Ser. No. 314,307, Oct. 23, 1981, Pat. No. 4,473,474, which is a continuation-in-part of Ser. No. 201,366, Oct. 27, 1980, abandoned.

[51] Int. Cl.$^4$ ............................................. B01D 13/00
[52] U.S. Cl. ................................................... 210/650
[58] Field of Search ........................ 210/649, 650, 651

[56] References Cited

U.S. PATENT DOCUMENTS

| | | | |
|---|---|---|---|
| T103,601 | 11/1983 | Repetti | 210/500.2 X |
| 2,539,768 | 1/1951 | Anderson . | |
| 2,783,894 | 3/1957 | Lovell | 210/203 |
| 2,926,116 | 2/1960 | Keim | 162/164 |
| 2,926,154 | 2/1960 | Keim | 260/29.2 |
| 3,152,061 | 10/1964 | Nishihara | 204/296 |
| 3,158,532 | 11/1964 | Pall et al. . | |
| 3,224,986 | 12/1965 | Butler et al. | 260/9 |
| 3,242,073 | 3/1966 | Guebert et al. | 210/64 |
| 3,311,594 | 3/1967 | Earle, Jr. | 260/77.5 |
| 3,332,901 | 7/1967 | Keim | 260/29.2 |
| 3,352,424 | 11/1967 | Guebert et al. | 210/502 |
| 3,382,096 | 5/1968 | Boardman | 117/139.5 |
| 3,408,315 | 10/1968 | Paine | 260/2.5 |
| 3,497,451 | 2/1970 | Hoehn et al. | 210/500 X |
| 3,556,305 | 1/1971 | Shorr | 210/490 |
| 3,556,992 | 1/1971 | Massuco | 210/23 |
| 3,567,631 | 3/1971 | Lukach | 210/23 |
| 3,585,107 | 6/1971 | Williams . | |
| 3,615,024 | 10/1971 | Michaels | 210/490 |
| 3,642,668 | 2/1972 | Bailey et al. | 260/2.5 M |
| 3,700,623 | 10/1972 | Keim . | |
| 3,761,350 | 6/1973 | Munjat et al. | 162/164 |
| 3,808,305 | 4/1974 | Gregor | 264/331 |
| 3,876,738 | 4/1975 | Marinaccio et al. | 264/41 |
| 3,928,517 | 12/1975 | Knight | 264/38 |
| 3,944,485 | 3/1976 | Rembaum et al. | 210/24 |
| 3,945,927 | 3/1976 | Imai et al. | 210/500.2 |

(List continued on next page.)

FOREIGN PATENT DOCUMENTS 0005536  11/1979  European Pat. Off. .

OTHER PUBLICATIONS

Ostreicher et al., U.S. application Ser. No. 164,797, filed Jun. 30, 1980.
Wallhauser, Journal of Parenteral Drug Association, Jun. 1979, vol. 33, #3, pp. 156–170.
Howard et al., Journal of Parenteral Drug Association, Mar.–Apr. 1980, vol. 34, #2, pp. 94–102.
Brown et al., CRC Critical Reviews in Environment Control, Mar. 1980, p. 279.
Wenk, Electronic and Chemical Aspects of Water Filtration, Filtration and Separation, May/Jun. 1974.

*Primary Examiner*—David Sadowski
*Attorney, Agent, or Firm*—Michael E. Zall

[57] ABSTRACT

A cationic charge modified microporous membrane comprising a hydrophilic organic polymeric microporous membrane and a cationic charge modifying agent bonded to substantially all of the wetted surfaces of the membrane, the charge modifying agent being an epichlorohydrin modified polyamide having tertiary amine or quaternary ammonium groups. A secondary charge modifying agent may be employed selected from: (i) aliphatic polyamines having at least one primary amine or at least two secondary amines; and (ii) aliphatic amines having at least one secondary amine and a carboxyl or hydroxyl substituent. Processes for producing and using the membrane are also described.

11 Claims, 3 Drawing Figures

U.S. PATENT DOCUMENTS

| | | | |
|---|---|---|---|
| 3,951,815 | 4/1976 | Wrasidlo | 210/500 M |
| 3,992,251 | 11/1976 | Lipowski | 162/164 EP |
| 4,005,012 | 1/1977 | Wrasidlo | 210/500.2 |
| 4,007,113 | 2/1977 | Ostreicher | 210/23 R |
| 4,007,114 | 2/1977 | Ostreicher | 210/23 R |
| 4,012,324 | 3/1977 | Gregor | 210/500 |
| 4,014,798 | 3/1977 | Rembaum | 210/500.2 |
| 4,045,352 | 8/1977 | Rembaum et al. | 210/500.2 |
| 4,125,462 | 11/1978 | Latty | 210/500.2 X |
| 4,142,020 | 2/1979 | Okamura et al. | 210/500.2 X |
| 4,148,606 | 4/1979 | Morita et al. | 422/21 |
| 4,176,156 | 11/1979 | Asanuma et al. | 422/25 |
| 4,178,438 | 12/1979 | Hasse et al. | 536/30 |
| 4,203,847 | 5/1980 | Grandine | 210/490 |
| 4,203,848 | 5/1980 | Grandine | 210/490 |
| 4,214,020 | 7/1980 | Ward et al. | 427/296 |
| 4,230,573 | 10/1980 | Kilty et al. | 210/767 |
| 4,239,714 | 12/1980 | Sparks et al. | 264/45.5 |
| 4,247,498 | 1/1981 | Castro | 264/41 |
| 4,250,029 | 2/1981 | Kiser et al. | 210/652 |
| 4,305,782 | 12/1981 | Ostreicher et al. | 162/181 C |
| 4,340,479 | 7/1982 | Pall | 210/490 |
| 4,411,795 | 10/1983 | Olson | 210/679 |
| 4,473,474 | 9/1984 | Ostreicher et al. | 210/636 |
| 4,473,475 | 9/1984 | Barnes, Jr. et al. | 210/639 |

OTHER PUBLICATIONS

Tanny et al., Journal of the Parenteral Drug Assoc., Nov.-Dec. 1978, vol. 32, #6, pp. 258-267.

Tanny et al, Journal of the Parenteral Drug Association, Jan.-Feb., 1979, vol. 33, #1, pp. 40-51.

Lukaszewicz et al., Journal of Parenteral Drug Association, Jul.-Aug. 1979, vol. 33, #4, pp. 187-194.

Pall et al., Colloids and Surfaces 1 (1980), pp. 235-256.

Zierdt, Charles, "Adherence of Bacteria . . . ", Applied and Environmental Microblgy., Dec. 1979, pp. 1166-1172.

Ostreicher, U.S. application Ser. No. 358,822, filed May 9, 1973.

Deutsch et al., "Isolation of Lipids from Plasma by Affinity Chromatography", Biochemical & Biophysical Research Communications, vol. 50, #3, 1973, pp. 758-764.

Hofstee, "Hydrophobic and Other Non-Ionic Paxameters in Protein, Separation and Adsorptive Immobilization by Substituted Agacoses," Polymer Science and Technology, vol. 16, Polymene Separation Media, edited by Anthony R. Cooper, copyright 1982 (a collection of manuscripts based on presentations at a symposium, Polymeric Separation Media, organized for the Second Chemical Congress of the North American Continent, held in Las Vegas, Aug. 24-29, 1980) pp. 87-92.

Knight, R. A., et al., "Microporous Membranes as Depth Filters", World Filtration Congress III, 9/13 to 17/1982.

9000 MAGNIFICATION

18000 MAGNIFICATION

LIQUID FILTRATION USING HYDROPHILIC CATIONIC ISOTROPIC MICROPOROUS NYLON MEMBRANE

RELATED APPLICATIONS

This is a continuation of U.S. Ser. No. 314,307, filed on Oct. 23, 1981, now U.S. Pat. No. 4,473,474, which is a continuation-in-part of U.S. Ser. No. 201,366, filed on Oct. 27, 1980, now abandoned. The entire disclosures of both of these applications are incorporated herein by reference.

This application is also related to copending application U.S. Ser. No. 268,543 filed May 29, 1981 entitled CHARGE MODIFIED MICROPOROUS MEMBRANE, PROCESS FOR CHARGE MODIFYING SAID MEMBRANE, AND PROCESS FOR FILTRATION OF FLUID to Barnes, Jr. et al. now U.S. Pat. No. 4,473,475. This copending application and the content thereof is not prior art with respect to the invention described and claimed in this application.

BACKGROUND OF THE INVENTION

1. Field of the Invention

This invention relates to microporous membranes, and more particularly to cationic charge modified microporous membranes suitable for the filtration of aqueous fluids, such as biological liquids.

2. Prior Art

Microporous membranes are well known in the art. For example, U.S. Pat. No. 3,876,738 to Marinaccio et al (1975) describes a process for preparing a microporous membrane, for example, by quenching a solution of a film forming polymer in a non-solvent system for the polymer. European Patent Application No. 0 005 536 to Pall (1979) describes a similar process.

Other processes for producing microporous membranes are described, for example, in the following U.S. Pat. Nos.: 3,642,668 to Bailey et al (1972); 4,203,847 to Grandine, II (1980); 4,203,848 to Grandine, II (1980); and 4,247,498 to Castro (1981).

Commercially available microporous membranes, for example, made of nylon, are available from Pall Corporation, Glen Cove, N.Y. under the trademark ULTIPOR $N_{66}$. Another commercially significant membrane made of polyvinylidene fluoride is available from Millipore Corp., Bedford, Mass. under the trademark Durapore. This membrane is probably produced by the aforementioned Grandine, II patents. Such membranes are advertised as useful for the sterile filtration of pharmaceuticals, e.g. removal of microorganisms.

Various studies in recent years, in particular Wallhausser, Journal of Parenteral Drug Association, June, 1979, Vol. 33, #3, pp. 156-170, and Howard et al, Journal of the Parentral Drug Association, March-April, 1980, Volume 34, #2 pp. 94-102, have reported the phenomena of bacterial break-through in filtration media, in spite of the fact that the media had a low micrometer rating. For example, commercially available membrane filters for bacterial removal are typically rated as having an effective micrometer rating for the microreticulate membranes structure of 0.2 micrometers or less, yet such membrane typically have only a 0.357 effective micrometer rating for spherical contaminant particles, even when rated as absolute for *Ps. diminuta*, the conventional test for bacterial retention. Thus passage of a few microorganisms through the membrane may be expected under certain conditions and within certain limits. This problem has been rendered more severe as the medical uses of filter membranes increases.

Brown et al highlights this problem in CRC Critical Reviews in Environmental Control, March 1980, page 279 wherein increased patient mortality and morbidity derived from contamination of sterile solutions for topical, oral, and intravenous therapy are reported.

One method of resolving this problem and its inevitable consequences, is to prepare a tighter filter, i.e. one with a sufficiently small effective pore dimension to enable the capture of microorganisms, bacterial pyrogen and viral contaminants, by mechanical sieving. Such filter structures, in the form of microporous membranes of 0.1 micrometer rating or less, may be readily prepared. The flow rates, however, exhibited by such structures at conventional pressure drops are prohibitively low. Generally, increasing the pressure drop to provide the desired flow rate is not feasible, even with costly replacement or modification of existing pumping equipment, due to the fact that pressure drop in an inverse function of the fourth power of pore diameter. Thus such a modification of the internal geometry, i.e. pore size, of the microporous membrane is not an economical solution to the problem of bacterial break-through.

It has long been recognized that adsorptive effects can enhance the capture of particulate contaminants. For example, Wenk in his article "Electrokinetic and Chemical Aspects of Water Filtration", Filtration and Seperation, May/June 1974, indicates that surfactants, PH, and ionic strength may be used in various ways to improve the efficiency of a filter by modifying the charge characteristics of either the suspension, filter or both.

It has also been suggested that adsorptive sequestration, i.e. adsorptive capture of particles by entry into and capture within the pore channels, may in some cases be more important to so-called sterile filtration than bubble point characterization of internal geometry (representing the "largest pore"). Tanny et al, Journal of the Parenteral Drug Association, November-December 1978, Vol. 21, #6 pp. 258-267 demonstrated that adsorptive effects dominate the filtration of flu vaccine through membranes of mixed cellulose esters, cellulose triacetate, and vinyl chloride-acrylonitrile copolymer, counter to the then common understanding of filtration as involving particulate removal by sieve-retention. This is consistent with the observation that bacterial pyrogen and virus particles may be removed by filtration through a membrane even though they are smaller than the pore sizes of commonly used 0.22 micrometer filters. Tanny et al, Journal of the Parenteral Drug Association, January-February, 1979, Vol. 33, #1, pp. 40-51.

Lukaszewicz et al, Journal of the Parenteral Drug Association, July-August, 1979, Vol. 33, #4, pp. 187-194, expanded on the foregoing and indicated that adsorptive particle arrest was a complex pheomenon. In discussing the effect of solution ionic strength on adsorptive particle arrest, Lukaszewicz et al indicated that high ionic strength tends to decrease adsorption, (thus reducing capture efficiency) if the attractive forces are due to electro-static interactions, i.e. the charge on the wall is opposite the charge on the particle.

Pall et al, Colloids and Surfaces 1 (1980), pp. 235-256, indicates that if the zeta potential of the pore walls of a membrane, e.g. nylon 66, and of the particles are both low, or if they are oppositely charged, the particle will tend to adhere to the pore walls, and the result will be removal of particles smaller than the pores of the filter. Pall et al, however, suggests the use of membranes of substantially smaller pore size to increase the probability of obtaining microbial sterility in filtering fluids.

Zierdt, Applied and Environmental Microbiology, December 1979, pp. 1166–1172, found a strong adherence by bacteria, yeast, erythrocytes, leukocytes, platelets, spores, and polystyrene spheres to membrane materials during filtration through membranes with pore-size diameters much larger than the particles themselves. Zierdt attributed this phenomena to electrostatic forces. The phenomena was partially blocked by pretreating the filter membrane with a nonionic surfactant. Zierdt found that cellulose membranes adsorbed more bacteria, blood cells and other particles then did polycarbonate filters. Of lesser adsorptive capacity were vinyl acetate, nylon, acrylic, and Teflon membranes. Zierdt additionally found that solvent cast membrane filter materials, e.g. nylon had strong surface charges, whereas ordinary fibrous cellulose materials which are not solvent cast do not. Zierdt suggested that the development and manufacture of special purpose filter materials with more intrinsic charge than those currently available would extend the usefulness of this phenomenon. Conversely, manufacturing techniques could be developed that would build less intrinsic charge into filters when adsorption is not desired.

Attempts to increase the short life of filter media due to pore blockage and enhance flow rates through filter media having small pores have been made by charge modifying the media by various means to enhance capture potential of the filter. For example, U.S. Pat. Nos. 4,007,113 and 4,007,114 to Ostreicher, describe the use of a melamine formaldehyde cationic colloid to charge modify fibrous and particulate filter elements; U.S. Ser. No. 147,975 filed May 8, 1980, now U.S. Pat. No. 4,305,782, to Ostreicher et al describes the use of an inorganic cationic colloidal silica to charge modify such elements; and copending U.S. Ser. No. 164,797 filed June 30, 1980, now abandoned to Ostreicher et al, describes the use of a polyamido-polyamine epichlorhydrin cationic resin to charge modify such filter elements. None of these references teach or suggest charge modifying an organic polymeric microporous membrane, nor do any of the filtration media described therein, e.g. fiber and/or particulate, provide the advantages of such a membrane.

Similarly, U.S. Pat. Nos. 3,242,073 (1966) and 3,352,424 (1967) to Guebert et al, describe the removal of micro-organisms from fluids by passing the fluids through a filter medium which comprises a conventional anionic type filter aid, e.g., diatomaceous earth, paper filter pulp, fullers earth, charcoal, etc., having an adsorbed cationic, organic, polyelectrolyte coating. The coated filter aid media is said to possess numerous cationic sites which are freely available to attract and hold particles bearing a negative surface charge.

U.S. Pat. No. 4,178,438 to Hasse et al (1979) describes a process for the purification of industrial effluent using cationically modified cellulose containing material. The cellulose containing materials are, for example, bleached or unbleached pine sulphite cellulose, kraft sulphate cellulose, paper, cardboard products, textiles fibers made of cotton, rayon staple, jute, woodfibers, etc. The cationic substituent is bonded to the cellulose via a grouping of the general formula $-O-CH_2-N-$, wherein the nitrogen belongs to an amide group of the cationic part and the oxygen to the cellulose part.

There are numerous references which describe the treatment of porous membranes for various objects. U.S. Pat. No. 3,556,305 to Shorr (1971) describes a tripartite membrane for use in reverse osmosis. The membrane comprises an anisoptropic porous substrate, an ultra-thin adhesive layer over the porous substrate, and a thin diffusive membrane formed over the adhesive layer and bound to the substrate by the adhesive layer. The anisotropic porous membranes used in Shorr are distinguished from isotropic, homogeneous membrane structures whose flow and retention properties are independent of flow direction. Such isotropic membranes do not function properly when utilized in the invention of Shorr.

U.S. Pat. No. 3,556,992 to Massuco (1971) describes another anisotropic ultra-filtration membrane having thereon an adhering coating of irreversibly compressed gell.

U.S. Pat. No. 3,808,305 to Gregor (1974) describes a charged membrane of macroscopic homogeneity prepared by providing a solution containing a matrix polymer, polyelectrolytes (for charge) and a cross-linking agent. The solvent is evaporated from a cast film which is then chemically cross-linked. The membranes are used for ultrafiltration.

U.S. Pat. Nos. 3,944,485 (1976) and 4,045,352 (1977) to Rembaum et al describe ion exchange hollow fibers produced by introducing into the wall of the preformed fiber, polymerizable liquid monomers. The monemers are then polymerized to form solid, insoluble, ion exchange resin particles embedded within the wall of the fiber. The treated fibers are useful as membranes in water-treatment, dialysis, and generally to separate ionic solutions. U.S. Pat. No. 4,014,798 to Rembaum (1977) describes similar type hollow fiber using different type resins to produce the ion exchange mechanism.

U.S. Pat. No. 4,005,012 to Wrasidlo (1977) describes a process for producing a semi-permeable anisotropic membrane useful in reverse osmosis processes. The membranes are prepared by forming a polymeric ultra-thin film, possessing semi-permeable properties on a microporous support. Such an ultra-thin film may be formed by contacting an amine modified polyepihalohydrin with a polyfunctional agent and depositing this film on the external surface of a microporous substrate. Preferred semipermeable membranes are polysulfone, polystyrene, cellulose butyrate, cellulose nitrate and cellulose acetate.

U.S. Pat. No. 4,125,462 to Latty (1978) describes a coated semi-permeable reverse osmosis membrane having an external layer or coating of a cationic polyelectrolyte preferably poly(vinylimidazoline) in the bi-sulfate form.

U.S. Pat. No. 4,214,020 to Ward et al (1980) describes a novel method for coating the exteriors of a bundle of hollow-fiber semipermeable membranes for use in fluid separations. Typical polymers coated are polysulfones, polystyrenes, polycarbonates, cellulosic polymers, polyamides and polyimides. Numerous depositable materials are listed, see col. 10, lines 55–col. 12, for example, poly(epichlorhydrin) or polyamides.

U.S. Pat. No. 4,239,714 to Sparks et al (1980) describes a method of modifying the pore size distribution of a microporous separation media so as to provide it with a sharp upper cut-off of a pre-selected molecular size. This is accomplished by effectively blocking the entrances to all of the pores of the separation media larger than a pre-selected molecular size constituting the desired cut-off, but leaving unchanged the smaller pores. The separation media may be in the form of polymeric membranes, e.g. cellulose acetate, cellulose nitrate, polycarbonates, polyolefins, polyacrylics, and polysulfones. The foregoing is accomplished by filling the pores of the membrane with a volatile liquid and then evaporating the liquid to form voids at the entrances to the pores. A concentrated solution of a cross-linkable or polymerizable pore blocking agent, such as protein, enzyme, or polymeric materials is then applied to the surface of the membrane.

U.S. Pat. No. 4,250,029 to Kiser et al (1981) describes coated membranes having two or more external coatings of polyelectrolytes with at least one oppositely charged adjacent pair separated by a layer of material which is substantially charge neutralized. Kiser et al is primarily directed to the use of charged membranes to repel ions and therby prevent passage through the membrane pores. The coated membranes are described as ordinary semi-permeable membranes used for ultrafiltration, reverse osmosis, electrodialysis or other filtration processes. A microscopic observation of the coated membranes shows microscopic hills and valleys of polyelectrolyte coating formed on the original external smooth skin of the membrane. The membranes are particularly useful for deionizing aqueous solutions. Preferred membranes are organic polymeric membranes used for ultra-filtration and reverse osmosis processes, e.g., polyimide, polysulfone, aliphatic and aromatic nylons, polyamides, etc. Preferred membranes are anisotropic hollow fiber membranes having an apparent pore diameter of from about 21 to about 480 angstroms.

Charge modified membranes are disclosed in U.S. Ser. No. 358,822 of Ostreicher filed May 9, 1973, now abandoned (corresponding to Japanese Patent No. 923649 and French Patent No. 74 15733). As disclosed therein, an isotropic cellulose mixed ester membrane, was treated with a cationic collidal melamineformaldehyde resin to provide charge functionality. The membrane achieved only marginal charge modification. Additionally, the membrane was discolored and embrittled by the treatment, extractables exceeded desirable limits for certain critical applications, and the membrane was not thermally sanitizable or sterilizable. Ostreicher also suggests such treatment for the nylon membranes prepared by the methods described in U.S. Pat. No. 2,783,894 to Lovell (1957) and U.S. Pat. No. 3,408,315 to Paine (1968). It has been demonstrated that nylon microporous membranes treated according to Ostreicher would also demonstrate marginal charge modification, high extractables and/or inability to be thermally sanitizable or sterilizable.

Of additional interest are the following U.S. Pat. Nos.: 3,497,451 to Hoehn et al (1970)—the use of "type 8" nylon for the desalination of sea water; 3,615,024 to Michaels (1968)—an anisotropic reverse osmosis membrane which may be nylon; 4,148,606 to Morita et al (1979)—a method of sterilizing a dialyzer by irradiating the semipermeable membrane in the presence of an antibacterial agent; and 4,176,156 to Asanuma et al (1979)—a method for heat sterilizing an artifical kidney.

OBJECTS AND SUMMARY OF THE INVENTION

It is an object of this invention to provide a novel cationic charge modified microporous membrane, particularly suitable for the filtration of biological or parenteral liquids.

It is a further object of this invention to provide a process for cationically charge modifying a hydrophilic organic polymeric microporous membrane.

It is still a further object of this invention to provide a process for the filtration of fluids, in particular the filtration of biological or parenteral liquids.

It is another object of this invention to provide an isotropic cationic charge modified microporous membrane which has low extractables suitable for the filtration of biological or parenteral liquids.

It is yet another object of this invention to prepare a sanitizable or sterilizable microporous membrane for the efficient removal of particulates, such as bacteria, viruses and pyrogen from contaminated liquids.

A still further object of this invention is to enhance the adsorptive sequestration capacity of microporous membranes without affecting the internal microreticulate structure.

It is a further object of this invention to enhance the capture potential of a preformed microporous membrane without decreasing the pore size of the membrane.

It is still a further object of this invention to provide a microporous membrane capable of capturing anionic particulate contaminant of a size smaller than the effective pore size of the membrane.

These and other object of this invention are attained by a novel cationic charge modified microporous membrane. The membrane comprises a hydrophilic organic polymeric microporous membrane and a charge modifying amount of a primary cationic charge modifying agent bonded to substantially all of the wetted surfaces of the membrane, the primary charge modifying agent being broadly and generally characterized as a water soluble organic polymer having a molecular weight greater than about 1000 wherein each monomer thereof has at least one epoxide group capable of bonding to the surface of the membrane and at least one tertiary amine or quaternary ammonium group.

Preferably the primary charge modifying agent is a polyamido-polyamine epichlorohydrin resin, a polyamine epichlorohydrin resin, or a resin based upon diallylnitrogen-containing materials reacted with epichlorohydrin. Such resins typically are the reaction product of a polyamine with epichlorohydrin and have (i) tertiary amine or quaternary ammonium groups, and (ii) epoxide groups along the polyamine chain capable of bonding to the microstructure of the membrane.

Preferably a portion of the epoxy groups on the organic polymer are bonded to a secondary charge modifying agent selected from the group consisting of:
 (i) aliphatic amines having at least one primary amine or at least two secondary amines; and
 (ii) aliphatic amines having at least one secondary amine and a carboxyl or hydroxyl substituent.

The invention is further directed to a process for cationically charge modifying a hydrophilic organic polymeric microporous membrane by applying to the membrane the aforesaid charge modifying agents. Preferably, the process for charge modifying the microporous membrane comprises contacting the membrane with aqueous solutions of the charge modifying agents.

The preferred microporous membrane is nylon, the preferred primary and secondary charge modifying agents are, respectively, polyamido-polyamine epichlorohydrin and tetraethylene pentamine.

The invention is further directed to a process for improving the responsiveness of a nylon membrane to charge modification, comprising chemically treating the membrane to provide enhanced ninhydrin response evidencing free amino functionality.

The charge modified microporous membrane of this invention may be used for the filtration of fluids, particularly parenteral or biological liquids.

DETAILED DESCRIPTION OF THE INVENTION

Figure 1:
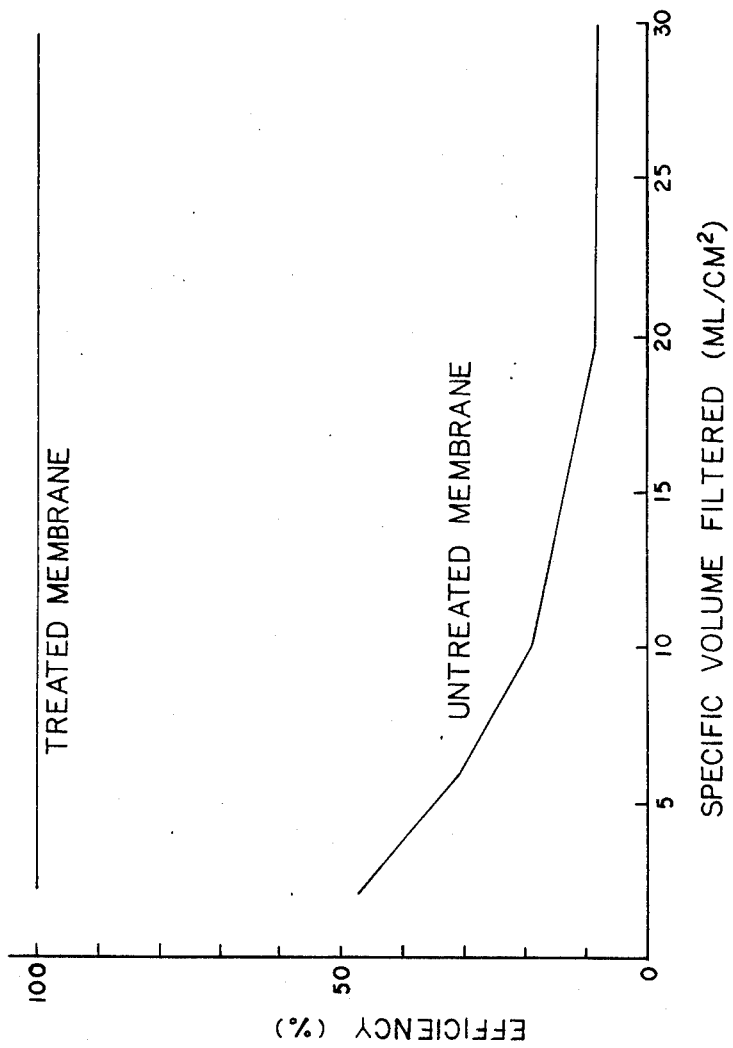
FIG. 1 is a graphical representation showing performance data, i.e. filtration efficiency, for a 0.2 micrometer membrane treated in accordance with the invention as compared to an untreated membrane, both challenged with 0.109 contaminant at 0.5 gpm/ft.$^2$ (0.002 lpm/cm$^2$) (See Example VII.)

The cationic charge modified microporous membrane of this invention is produced from a hydrophilic organic polymeric microporous membrane. Such membranes are well known in the art.

By the use of the term "microporous membrane" as used herein, it is meant a substantially symmetrical, isotropic porous membrane having a pore size of at least 0.05 microns or larger, e.g. at least 0.1 microns, or an initial bubble point (IBP), as that term is used herein, in water of less than 120 psi. A maximum pore size useful for this invention is about 1.2 micron or an IBP of greater than about 10 psi. By "symmetrical" it is meant that the pore structure is substantially the same on both sides of the membrane. A number of commercially available membranes not encompassed by the term "microporous membrane" are "asymmetric", i.e. having one side formed with a very light thin layer which is supported by a much more porous open structure. By the use of the term "isotropic", it is meant the membrane has a uniform pore structure throughout the membrane.

By the use of the term "hydrophilic" in describing the microporous membrane, it is meant a membrane which adsorbs or absorbs water. Generally, such hydrophilicity is produced by a sufficient amount of hydroxyl (OH—), carboxyl (—COOH) amino (—NH$_2$) and/or similar functional groups on the surface of the membrane. Such groups assist in the adsorption and/or absorption of the water onto the membrane. Such hydrophilicity of the membrane is a necessary element of this invention to provide the adequate bonding of the primary charge modifying agent through the epoxide substituent to the microporous membrane.

A preferred microporous membrane is one produced from nylon. The term "nylon" is intended to embrace film forming polyamide resins including copolymers and terpolymers which include the recurring amido grouping.

While, generally, the various nylon or polyamide resins are all copolymers of a diamine and a dicarboxylic acid, or homopolymers of a lactam of an amino acid, they vary widely in crystallinity or solid structure, melting point, and other physical properties. Preferred nylons for use in this invention are copolymers of hexamethylene diamine and adipic acid (nylon 66), copolymers of hexamethylene diamine and sebacic acid (nylon 610), and homopolymers of poly-o-caprolactam (nylon 6).

Alternatively, these preferred polyamide resins have a ratio of methylene (CH$_2$) to amide (NHCO) groups within the range about 5:1 to about 8:1, most preferably about 5:1 to about 7:1. Nylon 6 and nylon 66 each have a ratio of 6:1, whereas nylon 610 has a ratio of 8:1.

The nylon polymers are available in a wide variety of grades, which vary appreciably with respect to molecular weight, within the range from about 15,000 to about 42,000 and in other characteristics.

The highly preferred species of the units composing the polymer chain is polyhexamethylene adipamide, i.e. nylon 66, and molecular weights in the range above about 30,000 are preferred. Polymers free of additives are generally preferred, but the addition of antioxidants or similar additives many have benefit under some conditions.

The preferred membrane substrates are produced by the method disclosed in U.S. Pat. No. 3,876,738 to Marinaccio et al. Another method of producing such membranes is described in European Patent Application No. 0 005 536 to Pall (corresponding to U.S. Pat. No. 4,340,479). The entire disclosures of both of these references are incorporated herein by reference.

Additionally, any of the hydrophilic microporous membranes commercially available, for example, Pall Corp.'s ULTIPOR N$_{66}$ (nylon), Millipore's Durapore (polyvinylidene fluoride), and cellulose acetate/nitrate membranes produced by numerous companies, having characteristics potentially suitable for fine filtration of fluids, particularly aqueous systems, are suitable for treatment in accordance with this invention.

The Marinaccio et al process for producing membrane develops a unique fine internal microstructure through the quench technique described therein, offering a superior substrate for filtration. Broadly, Marinaccio et al produces microporous films by casting or extruding a solution of a film-forming polymer in a solvent system into a quenching bath comprised of a non-solvent system for the polymer. Although the non-solvent system may comprise only a non-solvent, the solvent system may consist of any combination of materials provided the resultant non-solvent system is capable of setting a film and is not deleterious to the formed film. For example, the non-solvent system may consist of materials such as water/salt, alcohol/salt or other solvent-chemical mixtures. The Marinaccio et al process is especially effective for producing nylon films. More specifically, the general steps of the process involve first forming a solution of the film-forming polymer, casting the solution to form a film and quenching the film in a bath which includes a non-solvent for the polymer.

The most important parameter responsible for development of micropores in the film, according to Marinaccio et al, is the solvent system employed with the polymer and the non-solvent system used in quenching the film. The selection of the solvent for the polymer is determined by the nature of the polymer material used and can be empirically determined on the basis of solubility parameters described in detail in Marinaccio et al.

The nylon solutions which can be used in the Marinaccio et al process include solutions of certain nylons in various solvents, such as lower alkanols, e.g., methanol, ethanol and butanol, including mixtures thereof. It is known that other nylons will dissolve in solutions of acids in which it behaves as a polyelectrolyte and such solutions are useful. Representative acids include, for example, formic acid, citric acid, acetic acid, maleic acid and similar acids which react with nylons through protonation of nitrogen in the amide group characteristic of nylon.

The nylon solutions after formation are diluted with non-solvent for nylon and the non-solvent employed is miscible with the nylon solution. Dilution with non-solvent may, according to Marinaccio et al, be effected up to the point of incipient precipitation of the nylon. The non-solvents are selected on the basis of the nylon solvent utilized. For example, when water-miscible nylon solvents are employed, water can be employed. Generally, the non-solvent can be methyl formate, aqueous lower alcohols, such as methanol and ethanol, polyols such as glycerol, glycols, polyglycols, and ethers and esters thereof, water and mixtures of such compounds. Moreover, salts can also be used to control solution properties.

The quenching bath may or may not be comprised of the same non-solvent selected for preparation of the nylon solution and may also contain small amounts of the solvent employed in the nylon solution. However, the ratio of solvent to non-solvent is lower in the quenching bath than in the polymer solution in order that the desired result be obtained. The quenching bath may also include other non-solvents, e.g., water.

The formation of the polymer film can be accomplished by any of the recognized methods familiar to the art. The preferred method is casting using a knife edge which controls the thickness of the cast film. The thickness of the film will be dictated by the intended use of the microporous product. In general, the films will be cast at thicknesses in the range of from about 1. mil. to about 20. mils., preferably from about 1 to about 10 mils.

Preferably, the polymer solution is cast and simultaneously quenched, although it may be desirable to pass the cast film through a short air evaporation zone prior to the quench bath. This latter technique is, however, not preferred.

After the polymer solution is cast and quenched, it is removed from the quench bath and preferably washed free of solvent and/or non-solvent. Subsequently the film can be at least partially dried and then treated in accordance with this invention.

Pall's aforementioned European Patent Application No. 0 005 536 describes another similar method for the conversion of polymer into microporous membrane which may be used. Broadly, Pall provides a process for preparing skinless hydrophilic alcohol-insoluble polyamide membranes by preparing a solution of an alcohol-insoluble polyamide resin in a polyamide solvent. Nucleation of the solution is induced by the controlled addition to the solution of a nonsolvent for the polyamide resin, under controlled conditions of concentration, temperature, addition rate, and degree of agitation to obtain a visible precipitate of polyamide resin particles (which may or may not partially or completely redissolve) thereby forming a casting solution.

The casting solution is then spread on a substrate to form a thin film. The film is then contacted and diluted with a mixture of solvent and nonsolvent liquids containing a substantial proportion of the solvent liquid, but less than the proportion in the casting solution, thereby precipitating polyamide resin from the casting solution in the form of a thin skinless hydrophilic membrane. The resulting membrane is then washed and dried.

In Pall's preferred embodiment of the process, the solvent for the polyamide resin solution is formic acid and the nonsolvent is water. The polyamide resin solution film is contacted with the nonsolvent by immersing the film, carried on the substrate, in a bath of nonsolvent comprising water containing a substantial proportion of formic acid.

These preferred nylon membranes, i.e. described in Marinaccio et al and Pall, are characterized by an isotropic structure, having a high effective surface area and a fine internal microstructure of controlled pore dimensions with narrow pore size distribution and adequate pore volume. For example, a representative 0.22 micrometer rated nylon 66 membrane (polyhexamethylene adipamide) exhibits an initial bubble point (IBP) of about 45 to 50 psid., a foam all over point (FAOP) of about 50 to 55 psid, provides a flow of from 70 to 80 ml/min of water at 5 psid (47 mm. diameter discs), has a surface area (BET, nitrogen adsorption) of about 13 $m^2/g$ and a thickness of about 4.5 to 4.75 mils.

The primary charge modifying agent used in this invention may broadly and generally be characterized as a water soluble organic polymer having a molecular weight greater than about 1000, wherein the monomer has at least one epoxide substituent capable of bonding to the surface of the membrane and at least one tertiary amine or quarternary ammonium group capable of providing a cationic charge site.

The primary charge modifying agent is bonded to substantially all of the wetted surface of the microporous membrane. By the use of the term "bonded" it is meant that the charge modifying agent(s) are sufficiently attached to the membrane and/or to each other so that they will not significantly extract under the intended conditions of use. By the use of the term "substantially all of the wetted surface" as used herein it is meant all of the external surface and internal pore surfaces which are wetted by a fluid passing through the membrane or in which the membrane is immersed.

Preferably the charge modifying agent is integral with the membrane surface, in the sense of extractables testing, i.e. the surface modified membrane structure is an integral coherent filter unit exhibiting less than 5 mg extractables in conventional testing.

The preferred charge modifier is selected from the class of polyamido-polyamine epichlorohydrin cationic resins, in particular, those described in the following U.S. Pat. Nos.: 2,926,116 to Keim; 2,926,154 to Keim; 3,224,986 to Butler et al; 3,311,594 to Earle, Jr.; 3,332,901 to Keim; 3,382,096 to Boardman; and 3,761,350 to Munjat et al.

The entire disclosures of all of these references are incorporated herein by reference. They may also be produced by conducting a polymerization of an allyl nitrogen-containing material reacted with epichlorohydrin.

Broadly, these preferred charge modifiers (hereinafter termed "polyamido-polyamine epichlorohydrin or polyamine epichlorohydrin") are produced by reacting a long chain polyamide with epichlorohydrin, i.e. 1-chloro-2,3 epoxypropane having the formula:

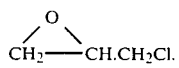

The polyamide may be derived form the reaction of a polyalkylene polyamine and a saturated aliphatic dibasic carboxylic acid containing from about 3 to 10 carbon atoms. The polyamide produced is water soluble and contains the recurring groups:

where n and x are each 2 or more and R is the divalent hydrocarbon radical of the dicarboxylic acid. This polyamide is then reacted with epichlorohydrin to form the preferred water soluble charge modifiers used in this invention.

The dicarboxylic acids which may be used in preparing the polyamides are the saturated aliphatic dicarboxylic acids containing from 3 to 10 carbon atoms each as malonic, succinic, glutaric, adipic, azelaic and the like. Blends, of two or more of the saturated carboxylic acids may also be used.

A variety of polyalkylene polyamines including polyethylene polyamines, polypropylene polyamines, polybutylene polyamides and so on may be employed. More specifically, the polyalkylene polyamines are polyamines, containing two primary amine groups and at least one secondary amine group in which the nitrogen atoms are linked together by groups of the formula $-C_nH_{2n}-$, where n is a small integer greater than unity and the number of such groups in the molecule ranges from two up to about eight. The nitrogen atoms may be attached to adjacent carbon atoms in the group $-C_nH_{2n}-$ or to carbon atoms further apart, but not to the same carbon atom. Polyamines such as diethylenetriamine, triethylenetetramine, tetraethylene-pentamine, dipropylenetriamine, and the like, and mixtures thereof may be used. Generally, these polyalkylene polyamines have the general formula:

$$H_2[(C_nH_{2n})NH]_yC_nH_{2n}NH_2$$

wherein n is an integer of at least 2 and y is an integer of 1 to 7.

In carrying out the reaction of the polyalkylene polyamine with the acid, it is preferred to use an amount of dicarboxylic acid sufficient to react substantially completely with the primary amine groups of the polyalkylene polyamine but insufficient to react with the secondary amine groups to any substantial extent. The polyamide produced is then reacted with the epichlorohydrin to form the preferred polyamido-polyamine epichlorohydrin charge modifying agent. Typically, in the polyamide-epichlorohydrin reaction it is preferred to use sufficient epichlorohydrin to convert all of the secondary amine groups to tertiary amine groups, and/or quaternary ammonium groups (including cyclic structures). Generally, however from about 0.5 mol to about 1.8 moles of epichlorohydrin for each secondary amine group of the polyamide may be used.

The epichlorohydrin may also be reacted with a polyaminoureylene containing teritiary amine nitrogens to produce the primary charge modifying agents which may be utilized in this invention (see for example the aforementioned Earle, Jr.).

Other suitable charge modifying agents of the foregoing type may be produced by reacting a heterocyclic dicarboxylic acid with a diamine or polyalkylene polyamine and reacting the resultant product with epichlorohydrin (see for example the aforementioned Munjat et al.)

The polyamido-polyamine epichlorohydrin cationic resins are available commercially as Polycup 172, 1884, 2002, or S2064 (Hercules); Cascamide Resin pR-420 (Borden); or Nopcobond 35 (Nopco). Most preferably the polyamido-polyamine epichlorhydrin resin is Hercules R4308, wherein the charged nitrogen atom forms part of a heterocyclic grouping, and is bonded through methylene to a depending, reactive epoxide group.

Each monomer group in R4308 has the general formula:

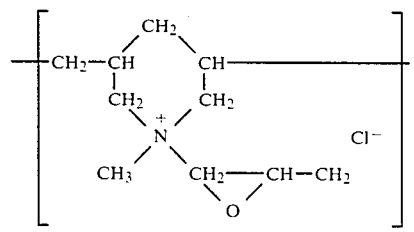

Polycup 172, 2002 and 1884, on the other hand, have monomer groups of the general formula:

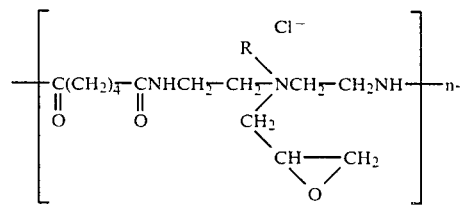

wherein R is methyl or hydrogen (Polycup 172 and 2002, R=H; and Polycup 1884, R=CH$_3$).

The improved charge functionality demonstrated by the preferred R4308 resin may be related to the nitrogen atoms partial removal from the polymer chain and consequent surface accessibility.

A secondary charge modifying agent or anchoring agent may be used to enhance the cationic charge of the primary charge modifying agent and/or enhance the bonding of the primary charge modifying agent to the microporous surface and/or itself.

The secondary charge modifying agent used in this invention is selected from the group consisting of:
 (i) aliphatic amines having at least one primary amine or at least two secondary amines; and
 (ii) aliphatic amines having at least one secondary amine and a carboxyl or hydroxyl substituent.

Preferably, the secondary charge modifying agent is a polyamine having the formula:

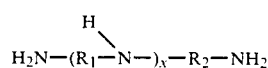

wherein $R_1$ and $R_2$ are alkyl of 1 to 4 carbon atoms and x is an integer from 0 to 4. Preferably, $R_1$ and $R_2$ are both ethyl.

Preferred polyamines are:
Ethylene diamine: $H_2N\text{-}(CH_2)_2\text{-}NH_2\text{-}NH_2$
Diethylenetriamine: $H_2N\text{-}(CH_2)_2\text{-}NH\text{-}(CH_2)_2\text{-}NH_2$
Triethylenetetramine: $H_2N\text{-}(CH_2\text{-}CH_2\text{-}NH)_2\text{-}CH_2\text{-}CH_2\text{-}NH_2$
Tetraethylenepentamine: $H_2N\text{-}(CH_2\text{-}CH_2\text{-}NH)_3\text{-}CH_2\text{-}CH_2\text{-}NH_2$ The highly preferred polyamine is tetraethylene pentamine.

Alternatively, aliphatic amines used in this invention may have at least one secondary amine and a carboxyl or hydroxyl substituent. Exemplary of such aliphatic amines are gamma-amino-butyric acid ($H_2NCH_2CH_2CH_2COOH$) and 2-aminoethanol ($H_2NCH_2CH_2OH$.)

The secondary charge modifying agent is bonded to the microporous membrane by bonding to a portion of the epoxide substituents of the polymeric primary charge modifying agent.

The amount of primary and secondary cationic charge modifying agent utilized is an amount sufficient to enhance the electropositive capture potential of the microporous membrane. Such an amount is highly dependent on the specific charge modifying agents utilized.

Broadly, the process of this invention is directed to cationically charge modifying a hydrophilic organic polymeric microporous membrane, e.g. nylon. The process comprises applying to the membrane a charge modifying amount of the primary cationic charge modifying agent bonded to the membrane structure through the epoxide substituent. Preferably, the process comprises (a) contacting the membrane with an aqueous solution of the primary cationic charge modifying agent and (b) contacting the membrane with an aqueous solution of the secondary charge modifying agent. The contacting steps may be performed in any order, i.e. step (a) prior to step (b) or vice versa. It is preferred, however, for optimum (minimum) extractables to first contact the membrane with an aqueous solution of the primary cationic charge modifying agent and then subsequently contact the so treated membrane with the aqueous solution of the secondary charge modifying agent.

In order to provide the charge modifying amount of cationic charge modifying agent to the membrane, it is preferred that the aqueous solution of primary charge modifying agent that the membrane is contacted with contain at least about 1.0% charge modifying agent, by weight of the solution. The maximum amount of charge modifying agent in the aqueous solution is limited by economic and solubility limitations. For example, an excess of primary charge modifying agent which is not bonded to the microporous membrane will not be economically utilized and will constitute an undesirable extractive from the membrane. It has been found that the amount of charge modifying agent in the aqueous solution should probably not exceed about 5% by weight of the solution.

The amount of secondary charge modifying agent used in the aqueous solution is highly dependent on the specific secondary charge modifying agent and the amount and type primary charge modifying agent used, and the cross-linking mechanism between these compounds to provide the bonding of such charge modifying agent to the microporous membrane. For general guidance however, it has been found that a weight ratio of primary to secondary charge modifying agent of from about 2:1 to about 500:1, preferably from about 25:1 to about 75:1 in the aqueous solutions contacted with the membrane, is generally sufficient to provide the bonding of the cationic charge modifying agents to the membrane. It has been found that if the aqueous solution containing the secondary charge modifying agent contains at least about 0.01% charge modifying agent by weight of the solution, up to a maximum of about 0.5% weight of the solution when used in conjunction with the aforementioned aqueous solution of primary charge modifying agent, that adequate bonding of the charge modifying agents to the microporous membane is obtained.

Both the charge modifying agents may be contacted with the membrane by dipping the membrane in the aqueous solutions of these compounds for a period of time sufficient to effect the desired degree of pick-up. Alternatively, the charge modifying agents may be applied by spraying or contacting a wick or roll along the surface of the microporous membrane.

Preferably, the hydrophilic membranes, in particular the nylon membrane produced according to the aforementioned Marinaccio et al, are surface activated, as with a caustic or basic wash, i.e. above pH 7, to provide a surface affording an enhanced amino-functionality as measured, for example, by ninhydrin colorimetery. This provides improved responsiveness to charge modification.

In an embodiment of this invention the membrane is surface activated before contacting charge modifying agents with the membrane. In the simplest form, the preferred nylon membrane is treated with caustic to provide additional amino groups for cross-linking. The same or enhanced effect is preferably achieved by providing an alkaline bath for application of at least one of the charge modifying agents, preferably the primary charge modifying agents. The bath is preferably at a pH of about 9 to about 11.

It is believed that the foregoing caustic surface treatment provides surface functionality free of blocking salts which are produced, for example, by the reaction of the acids used in producing the hydrophilic membrane (see, for example, Marinaccio et al and Pall) with the functional substituents, e.g. amino. Thus the caustic treated nylon membrane evidences an enhanced ninhydrin test response for free amino functionality.

For example, nylon 66 is made from adipic acid ($HOOC(CH_2)_4COOH$) and hexamethylene diamine ($NH_2(CH_2)_6NH_2$). Reaction of these two materials results in nylon 66 with the following repeating unit:

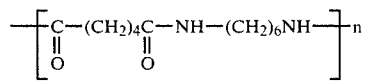

In acid solution (formic acid), as used in Marinaccio et al and Pall, the polymer acts as a polyelectrolyte, i.e. in formic acid solution the polymer chain acquires a charge. This charge results from the reaction of formic acid with the polymer. Specifically a proton ($H^+$) from the acid attaches to the nitrogen atom in the polymer chain yielding the following type charged structure:

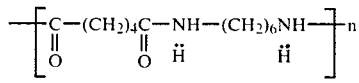

Since electrical neutrality is always maintained, each charge site (i.e.

is associated with the corresponding formate anion (HCOO$^-$). After the polymer is prepared and dried the salt structure is probably still present. It is theorized that these salts are neutralized by caustic or basic treatment used in this invention. It is believed that the high pH tends to activate the epoxide functionally on the primary charge modifying agent and break the formic acid/nylon amino bonds on the nylon surface and render the carboxylic acid groups on the nylon surface more reactive.

The activated expoxide groups of the primary charge modifying agent then react with both nylon functional groups, i.e., amino and carboxylic.

Although applicants do not wish to be bound by the following theory, it is believed that in bonding the primary charge modifying agent to the microporous membrane the epoxide groups on the primary charge modifying agent enter into addition type reactions with the hydroxyl, carboxyl and primary and secondary amines, which are on the hydrophilic microporous membrane and the primary and secondary cationic charge modifying agents. These reactions may be represented as follows:

Hydroxyl

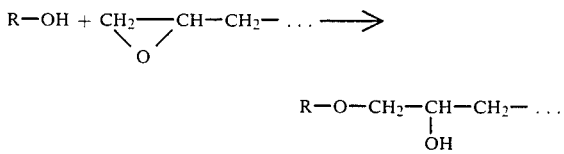

Carboxyl

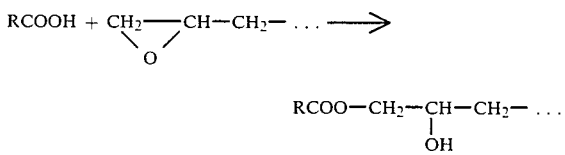

Primary Amine

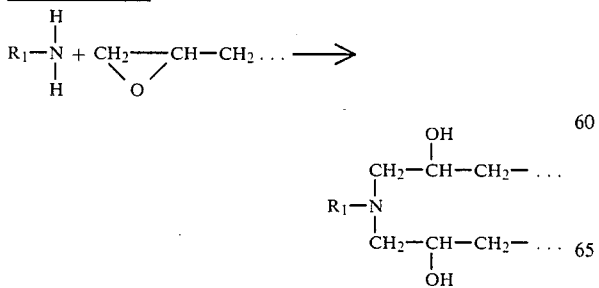

Secondary Amine

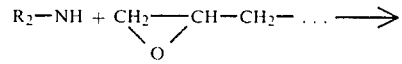

-continued

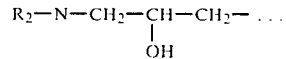

The epoxide substituent on the primary charge modifying agent thus serves several functions:

1. The epoxide cross-links the primary amine groups on the hydrophilic membrane to the primary charge modifying agent and the primary and/or secondary amine groups on the secondary charge modifying agent;
2. The epoxide cross-links the carboxyl groups on the hydrophilic microporous membrane to the primary charge modifying agent and the primary and/or secondary amine groups of the secondary charge modifying agent;
3. The epoxide cross-links the primary and/or secondary amines of the secondary charge modifying agent to each other.

It is theorized that a polymeric primary charge modifying agent offering greater than three epoxide groups per monomer offers no benefit, and in fact may limit the coupling reactions of the primary charge modifying agent by steric hindrance. Additionally, the presence of unreacted epoxide groups on the charge modified microporous membrane may be undesirable in the finished charge modified membrane.

The amines used as secondary charge modifying agents in this invention are selected in the view of the following theoretical considerations. Amines are classified as primary, secondary or tertiary, according to the number of substituents attached to the nitrogen atom, i.e. according to the number of hydrogens which have been substituted:

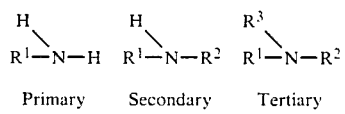

Primary   Secondary   Tertiary

Epoxide groups will react with primary and secondary amine groups through the free hydrogens. An epoxide group will not react with a tertiary amine group since there are no free hydrogens.

Amine groups of all three classes, i.e. primary, secondary or tertiary are capable of forming hydrogen bonds with water. As a result, amines of relatively low molecular weight, i.e. short carbon chain length are quite soluble in water, with border line solubility in water occurring at about 6 carbon atoms per amine group. In the preferred embodiment of this invention it is highly desirable that the cationic charge modifying agents be soluble in water to provide the desired environment for production, i.e. elimination of fumes, toxicity, etc.

Amines are basic and generally form salts:

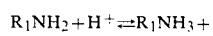

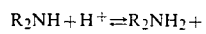

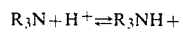

The amines are converted into their salts, i.e. charged form, by hydrogen ions and are liberated from their salts by hydroxide ions:

| | |
|---|---|
| $R_1NH_2 + H_3O+$ | $R_1NH_3 + H_2O$ |
| Stonger Base | Weaker Base |
| $R_1NH_3+ + OH^-$ | $R_1NH_2 + H_2O$ |
| Stronger Base | Weaker Base |

It is this latter characteristic, that produces an undesirable reduction in positive surface charge on the microporous membrane (as measured by electrophoretic mobility or streaming potential), and the corresponding reduction in adsorptive capacity for anionic contaminants that has been noted when amine charge modified filter media is tested over a series of increasing pHs. It would therefore appear that the more basic the amine charge modifying agent, the higher is the charge modification and adsorptive capacity for contaminants that a filter media, e.g. membrane, will exhibit at a given pH.

Basicity of an amine is defined by measuring the extent to which the amine can accept hydrogen ions from water, with the equilibrium constant for this reaction being the basicity constant Kb:

$$R_1NH_2 + H_2O \rightleftharpoons R_1NH_3^+ + OH^-$$

$$Kb = \frac{[R_1NH_3^+][OH^-]}{[R_1NH_2]}$$

From the literature, we find that aliphatic amines of all three classes, i.e. primary, secondary and tertiary, have Kb's that range from about $10^{-3}$ to $10^{-4}$, and are stronger bases than ammonia. This 10 to 1 range of Kb for aliphatic amines indicates that some amines will be better charge modifiers (high Kb) than others (low Kb). It is theorized that aromatic amines, which are considerably weaker bases than ammonia, having a Kb of $10^{-9}$ or less, are unsuitable as charge modifying agents.

To select from among the aliphatic amines a preferred embodiment on a theoretical basis becomes somewhat more complicated due to the fact that one is concerned with the basicity of the amine bonded through the epoxide to the microporous membrane.

From certain tests performed however, it appears that increased cross-linking with the epoxide substituent increases basicity and filtration effectiveness and thus appears to depend upon the extent to which the primary and secondary amines originally present in, for example, the tetraethylene pentamine, are converted to tertiary amines via the reaction with the epoxide.

Preferably, between each contacting step of the process for producing the membrane, the membrane is drained for a period of time sufficient to remove most of the water and chemical compound not absorbed or adsorbed onto the surface of the membrane. Optionally, the membrane may be transferred directly from the first contacting step to the second contacting step, although this is less preferred. The intermediate treatment may also be a restrained drying step.

After the microporous membrane has been contacted with the aqueous solutions, it is then dried and cured, preferably in a restrained condition to prevent shrinkage.

Drying of the membrane under restraint is described in the Assignee's co-pending U.S. Ser. No. 201,086 to Repetti filed Oct. 27, 1980 now Defensive Publication T-103,601. The entire disclosure of this application is incorporated herein by reference. Generally, any suitable restraining technique may be used while drying, such as winding the membrane tightly about a drying surface, e.g. a drum. Biaxial control is preferred and tensioning the membrane on a stretching frame is considered the most preferred. Preferably, the restraint imposed affects no reduction in dimensions.

Final drying and curing temperatures should be to dry and cure the treated membranes, preferably from about 120° C. to 140° C. for minimization of drying times without embrittlement or other detrimental affects to the membrane.

The completed membrane may be rolled and stored for use under ambient conditions. It will be understood that the treated membrane may be supplied in any of the usual commercial forms, for example, as discs or pleated cartridges.

The present invention provides an integral, coherent microporous membrane of retained internal pore geometry. The charge modified membrane has an improved effective filtration rating relative to the untreated micro-reticulate polymer structure. Such improvement is brought about by charge sites or regions which are effective during filtration to enhance filtration performance through eletrokinetic effects.

The resulting membrane offers improved micrometer rating at equivalent flow and capacity with retention of membrane structure, yet without evidence of significant resin extractables. In effect the effective micrometer rating for contaminant particles is less than the effective micrometer rating of the microreticulate membrane structure. By the use of the term "effective micrometer rating for contaminant particles", it is meant the actual size of the particles that the membrane will quantitatively remove from the fluid being filtered. By the use of the term "effective micrometer rating of the microreticulate membrane structure" it is meant the size of the particulate that would pass through the membrane if all adsorptive effects of the membrane were eliminated.

For so-called sterile filtrations involving biological liquids, the filter is sanitized or sterilized by autoclaving or hot water flushing. Accordingly, the charge modified membrane must be resistant to this type treatment, and must retain its integrity in use. Any modification to the filter structure, especially brought about by chemical agents which may be unstable under conditions of treatment and use, must be scrutinized with care to minimize the prospect of extractables contaminating the filtrate, interfering with analyses and potentially introducing harmful toxins to a patient. Specifically, any such filter must meet the test standards in the industry, e.g. ASTM D 3861-79 (incorporated herein by reference), and generally prove less than 5 mg. of extractables in 250 ml solvent (water at 80° C.; 35% ethanol at room temperature) for a 293 mm diameter disc.

While the primary and secondary charge modifying agents afford cross-linking functionality and cross-linking through such functionality with the base membrane, the improved accessibility of the reactive groups on the membrane brought about by the activation treatment, i.e. caustic wash, enhances interreaction of the agents with the membrane, and insures extremely low extraction levels. Where extraction levels are of major concern, this represents the most preferred embodiment.

The resulting charge modified membrane is characterized by retention of internal microstructure, thus offering essentially the same flow characteristics as the untreated membrane. For example, a 0.22 micrometer rated nylon membrane is essentially absolute for 0.109 test beads.

The charge modified membrane additionally is easy to handle and readily formed into convoluted structures, e.g. pleated configurations. By reason of its retained flow characteristics, it may be employed directly in existing installations, without pumping modifications. These favorable properties are secured without sacrifice to other characteristics. The membrane may also be constructed to meet or exceed extractable requirements.

Biological liquids as that term is employed in the specification and claims, is a liquid system which is derived from or amenable to use with living organisms. Such liquids are ordinarily handled and processed under sanitary or sterile conditions and therefore require sanitized or sterilized media for filtration. Included within such term are isotonic solutions for intermuscular (im) or intravenous (iv) administration, solutions designed for administration per os, as well as solutions for topical use, biological wastes or other biological fluids which may comprise filterable bodies such as impurities, e.g., bacteria, viruses or pyrogens which are desirably isolated or separated for examination or disposal by immobilization or fixation upon or entrapment within filter media.

Filter membranes in accordance with this invention may be employed alone or in combination with other filter media to treat pharmaceuticals such as antibiotics, saline, solutions, dextrose solutions, vaccines, blood plasma, serums, sterile water or eye washes; beverages, such as cordials, gin, vodka, beer, scotch, whisky, sweet and dry wines, champagne or brandy; cosmetics such as mouthwash, perfume, shampoo, hair tonic face cream or shaving lotion; food products such as vinegar, vegetable oils; chemicals such as antiseptics, insecticides, photographic solutions, electroplating solutions, cleaning compounds, solvent purification and lubrication oils; and the like for retention of submicronic particles, removal of bacterial contaminants and resolution of colloidal hazes. Illustratively, in hospital usage, membrane filters are employed to concentrate abnormal exfoliated cells from a vaginal rinse, to isolate blood parasites from peripheral blood, or bacteria from serum or leucocytes and casts from urine.

In the case of preparation for use in sterile filtration, the membrane is thermally sanitized or sterilized as by treatment in an autoclave at 121° C. under 15 psig. for 1 hour, or hot water flushing at 85° F. for 1 hour.

Having now generally described this invention, the same will become better understood by reference to certain specific examples, which are included herein for the purposes of illustration only and are not intended to be limiting of the invention.

EXAMPLES

The following are the measurement and test procedures utilized in all the Examples.

Thickness

The dry membrane thickness was measured with a ½ inch (1.27 cm) diameter platen dial indicator thickness gauge. Gauge accuracy was +0.00005 inches (+0.05 mils).

Initial Bubble Point (IBP) and Foam-All-Over-Point (FAOP) Tests

At 47 mm diameter disc of the membrane sample is placed in a special test holder which seals the edge of the disc. Above the membrane and directly in contact with its upper face, is a perforated stainless steel support screen which prevents the membrane from deforming or rupturing when air pressure is applied to its bottom face. Above the membrane and support screen, the holder provides a inch deep cavity into which distilled water is introduced. A regulated air pressure is increased until a first stream of air bubbles is emitted by the water wetted membrane into the quiescent pool of water. The air pressure at which this first stream of air bubbles is emitted is called the Initial Bubble Point (IBP) of the largest pore in that membrane sample—see ASTM D-2499-66T.

Once the Initial Bubble Point pressure has been determined and recorded, the air pressure is further increased until the air flow thru the wetted membrane sample, as measured by a flow meter in the line between the regulator and the sample holder, reaches 100 cc/min. The air pressure at this flow rate, is called the Foam-All-Over-Point (FAOP), and is directly proportional to the mean pore diameter of the sample membrane. In this series of tests, these two parameters (IBP and FAOP) are used to determine if any change has occurred in the maximum or mean pore size of the membrane sample as a result of the charge modifying process utilized.

Flow Rate Test

A 47 mm diameter disc of the membrane sample is placed in a test housing which allows pressurized water to flow thru the membrane. Prefiltered water is passed thru the membrane sample at a pressure differential of 5 psid. A graduate cylinder is used to measure the volume of water passed by the membrane sample in a one minute period. In this series of tests this parameter is used in conjunction with the IBP and FAOP to determine if any reduction in pore size or pore blockage has occurred as a result of the charge modifying process utilized.

Dye Adsorption Test

A 47 mm diameter disc of the membrane sample is placed in a test housing which allows pressurized water flow thru the membrane. The challenge solution consists of distilled water at a pH of 7.0, and Metanil Yellow dye. The dye inlet concentration is adjusted to produce a 76 percent transmittance at a wavelength of 430 nm, as measured on a Perkin-Elmer Model 295 Spectrophotometer. By means of a peristaltic pump the challenge solution is flowed thru the membrane sample at a flow rate of 28 ml/min. The transmittance of the effluent is measured by passing it thru a constant flow cell in the aforementioned Spectrophotometer. The effluent transmittance and pressure drop across the membrane is measured and recorded as a function of time. The test is terminated when the effluent transmittance increases to 85 percent of the inlet transmittance. In this series of tests, the length of time that it takes to reach the 85 percent transmittance in the effluent is called the "breakthru" time. Since the Metanil Yellow is a low molecular weight anionic dye incapable of being mechanically removed (filtered) by the membrane, this breakthru time is proportional to the cationic adsorptive capacity of the membrane sample. This test is therefore used to determine the effectiveness of the charge modification technique.

Extractables (ASTM D-3861-79)

Extractables were determined by ASTM D-3861-79. The quantity of water-soluble extractables present in the membrane filters was determined by immersing the preweighed membrane in boiling reagent grade water for an extended time and then drying and reweighing the membrane. A control membrane was employed to eliminate weighing errors caused by balance changes or changing moisture content of the membrane in the weighing procedures. Weight changes of the control membrane were applied as a correction factor to the weight change of the test membrane filters.

EXAMPLE I

A

Preparation of Microporous Membrane

A representative nylon 66 membrane of 0.22 micrometer nominal rating, having a nominal surface area of about 13 m$^2$/g, an Initial Bubble Point of about 47 psi, a Foam-All-Over-Point of about 52 psi was prepared by the method of Marinaccio et al, U.S. Pat. No. 3,876,738, utilizing a dope composition of 16 percent by weight nylon 66 (Monsanto Vydyne 66B), 7.1% methanol and 76.9% formic acid, a quench bath composition of 25% methanol, 75% water by volume (regenerated as required by the method of Knight et al, U.S. Pat. No. 3,928,517) a casting speed of 24 inches/minute (61 cm/min), and a quench bath temperature of 20° C. The membrane was cast just under the surface of the quench bath by application to a casting drum rotating in the bath (9 to 10 mils as cast wet, to obtain 4.5 to 5.5 mils dry) and allowed to separate from the drum about 90° of arc from the point of application, the self-supporting membrane forming a shallow catenary to takeup. A portion of the uniform opaque film was dried (in restrained condition to resist shrinkage) in a forced air oven at 80°-90° C. for 30 minutes.

EXAMPLE I (Cont.)

B

Preparation of Charge Modified Microporous Membrane

1. Membrane samples (dried and undried) were dipped in a bath of Hercules 1884 polyamido-polyamine epichlorohydrin resin (4% solids by weight), and allowed to attain adsorption equilibrium. The treated membrane samples were washed to remove excess resin and dried in restrained condition on a drum at a temperature of 110° C. for a period of about 3 minutes.

The treated membrane samples were compared for flow and bubble point characteristics as follows, and found to be essentially identical for treated and untreated samples, evidencing retention of pore and surface geometry. The results are set forth in Table I.

TABLE I

|  | Control (No treatment) | Undried Membrane | Dried Membrane |
|---|---|---|---|
| Thickness (mils) | 4.25 | 4.58 | 4.83 |
| Initial Bubble Point (psi) | 43.7 | 44.7 | 44.7 |
| Foam-All-Over-Point (psi) | 55.0 | 54.0 | 54.7 |
| Thickness Normalized Flow Rate (cc. mil/min. cm$^2$ · psi) | 7.1 | 7.2 | 7.0 |
| BET, N$_2$ adsorption | 13.12 | — | 13.58 |

Thus, in terms of the morphological and hydrodynamic parameters that control mechanical sieving, the filtration characteristics of the treated memrbranes were essentially identical with the untreated nylon membrane.

2. Similar characterizations were conducted on another membrane sample, similarly prepared, but treated with 2% Hercules R4308 resin (a free radical polymerized resin based upon diallyl nitrogen-containing materials, reacted with epichlorohydrin) in a bath adjusted to pH 10.5, overcoated with 0.1% tetraethylene pentamine, dried, cured, washed and redried. The results are set forth in Table II.

TABLE II

|  | Control (No treatment) | Dried Membrane |
|---|---|---|
| Tensile Strength (psi) | | |
| Wet | 528 | 635 |
| Dry | 860 | 960 |
| Elongation (%) | | |
| Wet | 140 | 100 |
| Dry | 95 | 40 |

Surface area of the treated and untreated membranes remained essentially unchanged; tensile strength increased with treatment with some loss in elongation. The treated sheet was more flexible; creasing of the untreated sheet resulted in cracking and splitting.

EXAMPLE I (Cont.)

C

Filtration Tests

The Hercules 1884 treated membrane samples (Example I.B.1.) were subjected to the filtration tests indicated below:

Pyrogen Removal

Purified E. coli endotoxin was added to a 0.9% NaCl solution, pH 6.7 and passed through test filters mounted in a 25 mm diameter stainless steel holder. Inlet and effluent endotoxin levels were determined by standard L.A.L. analysis.

Results are set forth in Table III.

TABLE III

| Filter | Inlet Endotoxin Level (pg/ml) | Effluent Endotoxin Level (pg/ml) | | |
|---|---|---|---|---|
| | | 10 ml. | 50 ml | 100 ml |
| Dried, treated Membrane | 15000 | 1000 | 1000 | 1000 |
| Control-Untreated | 15000 | 10000 | 10000 | 10000 |

(Pg is "picogram")

Virus Removal

MS-2 bacteriophage was added to Houston, Tex. (U.S.A.) tap water to produce a concentration of 3.4×105 PFU/ml PFU is "Plaque Forming Unit"),, and 10 ml was passed through each of the test filters mounted in a 25 mm diameter stainless steel holder. Effluents were analyzed for viral content by standard techniques. Results are set forth in Table IV:

TABLE IV

| Filter | Total Viral PFU in Filtrate | Vicus Removal Efficiency (%) |
|---|---|---|
| Dried, treated Membrane | 100 | 99.997 |
| Control-untreated | 250000 | 26.4 |

Monodisperse Latex Filtration

The test filters were challenged with a 10 NTU dispersion (NTU is "nephlometric turbiidity units") of 0.109 micrometer monodisperse latex (MDL) particles at a flow rate of 0.5 gpm/ft.$^2$ (0.002 lpm/cm$^2$), pH 7.0, R=21000-ohm-cm. Effluent turbidities (NTU) were monitored and filtration efficiencies were calculated from equilibrium effluent turbidities. Results are set forth in Table V.

TABLE V

| Filter | MDL Removal Efficiency |
|---|---|
| Undried, treated | 97.3% |
| Control-untreated | 10% |

Dye Removal Efficiency

The test filters were challenged with a solution of blue food coloring dye (FD & C No. 1). The solution had a light transmittance of 62.5% at 628 nm. The light transmittance of the effluent was monitored and removal efficiencies determined (based on distilled water light transmittance=100%). Results are set forth in Table VI.

TABLE VI

| | Throughput (liters) to 90% Transmittance |
|---|---|
| Undried, treated | 1.99 |
| Dried, treated | 1.76 |
| Control-untreated | 0 |

EXAMPLE II

In a series of related runs employing dried Hercules 1884 treated membrane as described in Example I.B.1. the amount of charge modifying resin in the treatment bath was modified from 1 to 5% by weight, the drying time for the treated membrane was altered from 15 to 30 minutes, the adsorption equilibration time was modified from 1 to 5 minutes, and pH was shifted from 4 to 9 and the factorial experiment analyzed for responses.

The results showed that as concentration of charge modifying resin increased, flow rate was adversely affected with increased pressure drop, while enhancing filtration performance as measured by dye retention time. This suggests some clogging of pores by resin at the higher levels. Higher extractions suggested the presence of excess resin at the 5% wgt. level.

Reduced extractables were evidenced for longer drying times and flow rate improved, with little change in pressure drop or filtration performance.

Longer equilibration time correlated favorably with reduced extractables, as well as improving flow rate at essentially equivalent pressure drop and filtration performance.

Alkaline pH conditions reduced extractables markedly, and the treated membrane showed improved flow rate and filtration at essentially equivalent pressure drop.

EXAMPLE III

A. A non-treated microporous nylon membane prepared in accordance with Example IA was soaked in ninhydrin (1,2,3-trione-2-hydrate, 0.4% aqueous) overnight, and examined for color development. The membrane had turned a light purple, evidencing a good level of amino functionality (positive test ranges from blue to purple). A competitive Pall Corp. nylon membrane (non-charge modified) evidenced only a very pale hint of lavender tint in the same test.

The same membrane of Example IA was washed with a saline solution and soaked in saturated sodium tetraborate. The membrane tested positive for amino-functionality (yellow to orange color) with the addition of 3-4 drops of 2,4,6-trinitro benzene sulfonic acid (3% aqueous). The solution turning a muted yellow within 30 seconds. The competitive Pall membrane showed no color response.

B. The untreated membrane of Example IA was treated with caustic (1 minute immersion in aqueous sodium hydroxide ph 10.5) washed, dried and soaked in ninhydrin overnight. The membrane was deeper purple than the untreated indicating for this test increased amino functionality. The competitive Pall nylon membrane, treated in the same manner, evidenced a light purple coloration, also indicating an increased amino functionality compared to the untreated membrane.

C. The membrane of Example IA treated with caustic was treated with Hercules resin R4308, dried, cured, washed and redried. Extractables testing (ASTM D 3861-79) evidenced reduced extractables as compared to a membrane treated with the same resin, but without caustic pretreatment.

EXAMPLE IV

A. Microporous nylon membrane prepared in accordance with Example IA was treated with a Hercules R 4308 primary charge modifying agent (pH of bath adjusted to 10 with sodium hydroxide) and, where indicated with a polyamine secondary charge modifying agent.

Flow characteristics of the respective membranes showed little or no differentiation, as set forth in Table VII:

TABLE VII

| TREATMENT | | | MEMBRANE CHARACTERISTICS | | |
|---|---|---|---|---|---|
| CHARGE MODIFIER | | | IBP$^1$ | FAOP$^2$ | THICKNESS NORMALIZED |
| PRIMARY | SECONDARY | SEQUENCE | (psi) | (psi) | FLOW$^3$ (cc. mil$^2$/min cm$^2$ psi) |
| None | None | — | 48.7 | 52.0 | 6.76 |
| 2.0% | 0.133% Anquamine$^4$ | Primary First | 47.3 | 52.3 | 6.76 |
| 2.0% | 0.133% Anquamine | Secondary First | 45.3 | 50.3 | 6.45 |
| 2.0% | 0.133% Anquamine$^4$ | Mixed | 48.7 | 51.3 | 6.05 |
| 2.0% | None | — | 46.7 | 51.0 | 7.25 |
| 2.0% | 0.03% Tetraethylene | Primary First | 49.5 | 54.0 | 5.80 |

TABLE VII-continued

| TREATMENT | | | MEMBRANE CHARACTERISTICS | | |
|---|---|---|---|---|---|
| CHARGE MODIFIER | | | IBP[1] | FAOP[2] | THICKNESS NORMALIZED |
| PRIMARY | SECONDARY | SEQUENCE | (psi) | (psi) | FLOW[3] (cc. mil$^2$/min cm$^2$ psi) |
| | Pentamine | | | | |

[1] Initial Bubble Point
[2] Foam All Over Point
[3] $\frac{\text{Flow rate (cc)} \times \text{thickness (mil)}}{(\Delta P \text{ (psid)}) \times \text{Area (cm}^2)}$
an empirically derived relation to normalize data for thickness variations.
[4] Anquamine - 100, a low molecular weight (under 10,000) cationic polyamide adduct evidencing secondary amine functionality by comparative UV spectroanalysis, supplied by Pacific Anchor Chemical Corp.

B. Filtration performance of the treated membranes was determined in a membrane life test, employing 0.109 monodisperse polystyrene latex from Dow Diagnostic (MDL) mixed with double glass distilled water to produce a dispersion with a turbidity of 10 NTU as measured on a Hach Model 2100A Turbidimeter. The pH of the test dispersion was 7.0.

Flow of contaminated dispersion at a rate of 14 ml/min. was established through a 47 mm. membrane test disc, and differential pressure and turbidity of effluent monitored. The test was deemed complete at 5 psid or attainment of 5 NTU contamination in the effluent. The performance is recorded as elapsed time. Results are set forth in Table VIII, as follows:

TABLE VIII

| TREATMENT | | | MDL TEST PERFORMANCE | | | | |
|---|---|---|---|---|---|---|---|
| CHARGE MODIFIER | | | INIT. ΔP | MAX. | AVG. | FINAL | TIME |
| PRIMARY | SECONDARY | SEQUENCE | (psi.) | NTU | NTU | ΔP(psi) | (Min.) |
| 2.0% | 0.133% Anquamine | Primary First | 0.70 | 5.1 | 1.35 | 1.4 | 60 |
| 2.0% | 0.133% | Secondary First | 0.90 | 5.1 | 1.34 | 1.7 | 60 |
| 2.0 | 0.133% | Mixed | 0.65 | 2.4 | 0.96 | 3.0 | 80 |
| 2.0% | NONE | Primary Only | 0.70 | 7.0 | 4.7 | 0.7 | 10 |
| 2.0% | 0.03 Tetraethylene pentamine | Primary First | 0.60 | 0.36 | 0.17 | 5.00 | 107 |

C. Filtration performance was also compared between samples of membrane treated with a bath containing either 4.24 wgt. % R 4308 or 2.45% R 4308, both followed by a bath of 0.03% tetraethylene pentamine. The two membranes performed equivalently in membrane life test with 0.109 MDL contaminant challenge. The latter membrane, which contained less primary charge modifier, performed better in dye retention tests.

D. The membranes were tested for extractables, in accordance with ASTM D-3861-79. The results are set forth in Table IX.

TABLE IX

| TREATMENT | | | EXTRACTIONS |
|---|---|---|---|
| CHARGE MODIFIER | | | PURSUANT TO |
| PRIMARY | SECONDARY | SEQUENCE | ASTM D-3861-79 |
| 2.0% 4308 | 0.133% Anquamine | Primary First | 0.0 mg |
| 2.0 4308 | 0.133% Anquamine | Secondary First | 3.5 |
| 2.0% 4308 | 0.133% Anquamine | Mixed | 4.7 |
| 2.0% 4308 | NONE | Primary Only | 0.0 mg |
| 2.0% 4308 | 0.03% tetraethylene pentamine | Primary First | 0.0 mg |

EXAMPLE V

In order to compare performance of different primary charge modifiers, particularly polyamide-polyamine epichlorohydrin resin candidates and to optimize application levels and pH conditions, the following tests were conducted, utilizing Hercules resins R4308 Polycup 172, pH 4.7 as supplied) and Polycup 2002 (27% solids, pH 3.0 as supplied). The results are set forth in Table X:

TABLE X

| Primary Charge Modifier | Bath pH | IBP | FAOP | Flow Rate ml/min. (20" Hg) | Initial ΔP | Final ΔP | Dye Ret.[1] Minutes |
|---|---|---|---|---|---|---|---|
| 1% R4308 | 10.3 | 47 | 50 | 162 | 1.85 | 4.4 | 68 |
| 2% R4308 | 10.3 | 45 | 49 | 162 | 1.80 | 4.4 | 100+ |
| 3% R4308 | 10.3 | 44 | 51 | 184 | — | 15.2 | 100+ |
| 1% 172 | 11.0 | 46 | 50 | 171 | 18.80 | 6.5 | 30 |
| 1% 172 | 4.9 | 47 | 50 | 162 | 2.10 | 2.2 | 15 |
| 2% 172 | 11.0 | 47 | 52 | 288 | — | 1.8 | 34 |
| 2% R4308 | 11.0 | 47 | 52 | 187 | — | 5.2 | 60 + |
| 2% 2002 | 11.0 | 49 | 52 | 183 | — | 2.5 | 35 + |

TABLE X-continued

| Primary Charge Modifier | Bath pH | IBP | FAOP | Flow Rate ml/min. (20" Hg) | Initial ΔP | Final ΔP | Dye Ret.[1] Minutes |
|---|---|---|---|---|---|---|---|
| Control | — | 46 | 50 | 267 | 1.90 | 2.9 | 5 |

[1]Metanil yellow at 1 ppm. The test was maintained until dye breakthrough, measured as 75% transmittance at 430 nanometers.

EXAMPLE VII

B

FIG. 1 is a graphical representation of Filtration Efficiency (%) versus the Specific Volume Filtered (ml/cm$^2$) for a charge modified membrane of this invention ("Treated Membrane") and a noncharge modified membrane ("Untreated Membrane"). Both membranes had a 0.2 micrometer rating prior to treatment. The charge modified membrane was produced by treating a nylon microporous membrane with a bath of 2% by weight of Hercules R4308 resin at a pH of 10.5 followed by a bath of 0.1% tetraethylene pentamine. Both the treated and untreated membranes were challenged with a 0.109 MDL contaminant at 0.5 gpm/ft$^2$.

B

Figure 2:
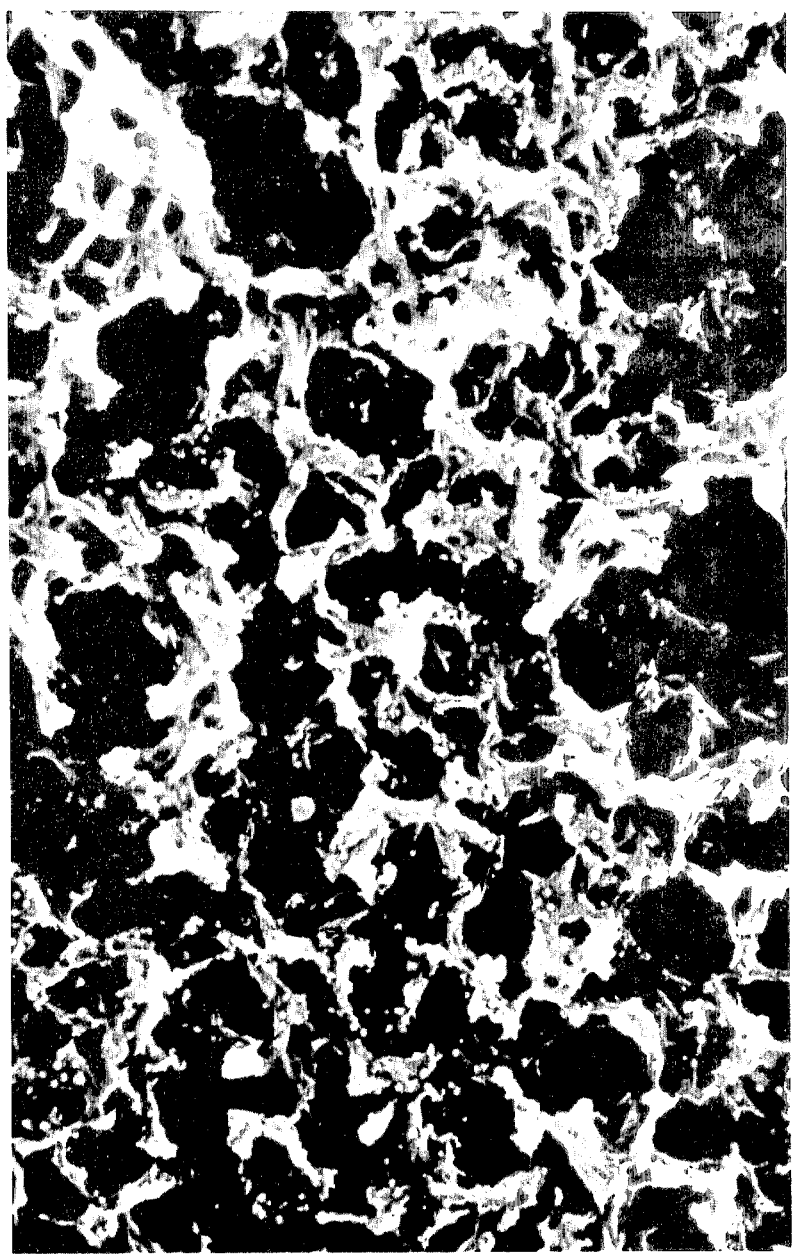
FIGS. 2 and 3 are Scanning Electron Microscope (SEM) photos of the cationic charge modified membrane of this invention challenged with contaminant (See Example VII.)
Figure 3:
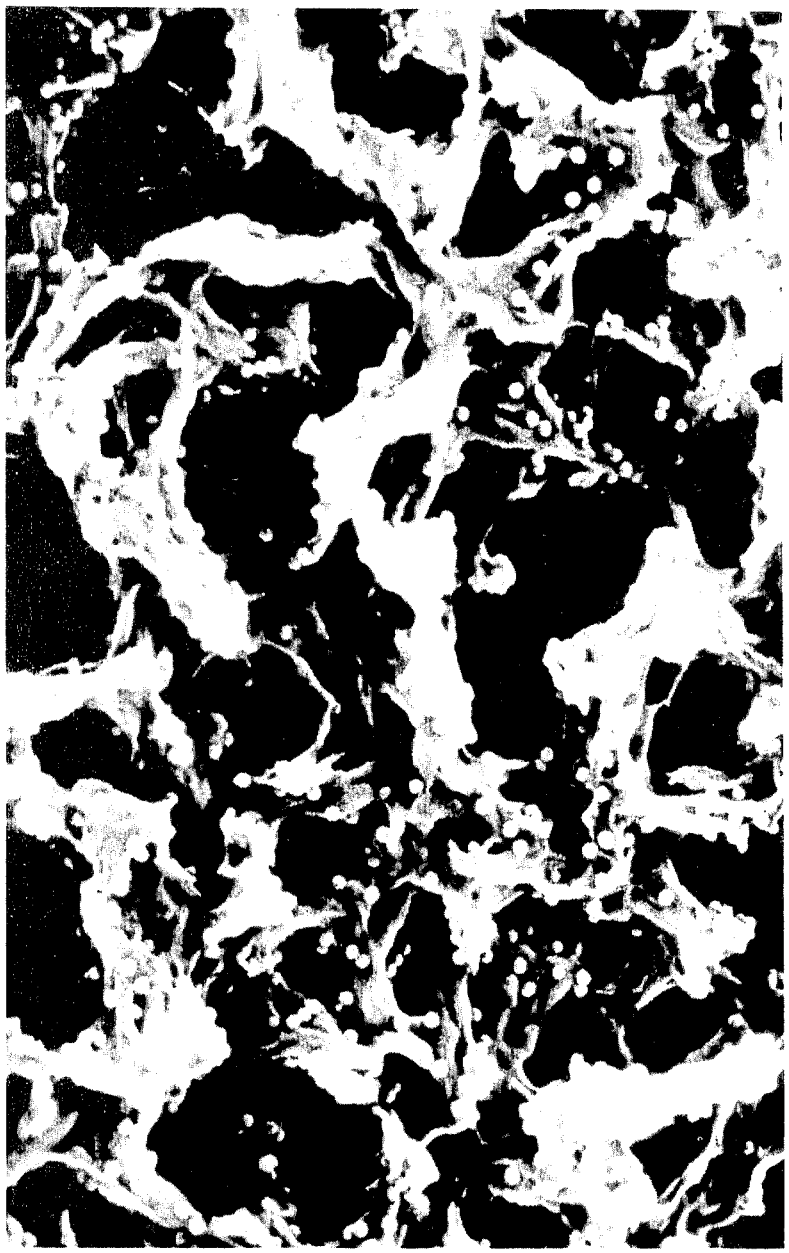

FIGS. 2 and 3 are Scanning Electron Microscope (SEM) photos of a charge modified membrane produced and challenged as described in this Example VII A with a 0.14 micron MDL beads (FIG. 2—7000X; FIG. 3—14,000X).

EXAMPLE VIII

A series of tests were conducted to investigate the characteristics of the charge modified membrane of this invention and process for producing such membrane.

The membrane used for this test series was a single sheet of unmodified, double layer, 0.2 um nylon membrane produced pursuant to the aforementioned Marinaccio et al patent (see Example IA). Each Sample group consisted of three (3) adjacent 21.6 cm×27.9 cm sheets, i.e. sheets "A", "B" and "C". The "A: sheet was left untreated and was used to provide data for "unmodified" or "before treatment" membrane. The "B" and "C" groups were subjected to the treatment modes given in Table XL. The "A" and "B" groups were subjected to the following measurements and tests:

Thickness—4 samples, 47 mm disc
Initial Bubble Point (IBP) and Foam-All-Over-Point (FAOP)—4 samples, 47 mm disc
Flow—4 samples, 47 mm disc
Dye Adsorption—2 samples, 47 mm disc
Extraction—10 samples, 293 mm disc per ASTM D-3861-79

The "C" group was retained for future testing.

The results obtained from the testing of the various treatment modes (see Table XI) are statistically summarized in Table XII.

TABLE XI

| NO. | PRETREATMENT | TREATMENT MODES CHARGE MODIFICATIONS | POST TREATMENT |
|---|---|---|---|
| 1 | NONE | Parez 607 Colloid-2 wt. % solution-PH as diluted | Drain and stretch dry |
| 2 | NONE | 1884 Resin-2 wt. % solution-pH as diluted | Drain and stretch dry |
| 3 | NONE | Wesol PA -2 wt. % solution-pH as diluted | Drain and stretch dry |
| 4 | NONE | 4308 Resin-2 wt. % solution-pH as diluted | Drain and stretch dry |
| 5 | Soak membrane in dilute NaOH solution (pH 10.5)for two minutes. Drain and oven dry. Wash in distilled water | Parez 607 Colloid-2 wt. % solution-pH as diluted | Drain and stretch dry |
| 6 |  | 1884 Resin-2 wt. % solution-pH as diluted | Drain and stretch dry |
| 7 |  | Wesol PA-2 wt. % solution-pH as diluted | Drain and stretch dry |
| 8 |  | 4308 Resin-2 wt. % solution-pH diluted. | Drain and stretch dry |
| 9 | NONE | 4308 Resin-2 wt. % solution-pH diluted | Drain and stretch dry |
| 10 | NONE | 4308 Resin-2 wt. % solution pH adjusted to 10.5 | 0.03 wt % solution Pentamine Drain and stretch dry |
| 11 | 0.03 wt. % solution Pentamine | 4308 Resin-2 wt. % solution pH as diluted | Drain and stretch dry |
| 12 | 0.03 wt. % solution (1.4 butanediol) | 1884 Resin-2 wt. % solution-pH as diluted | Drain and stretch dry |
| 13 | 0.03 wt. % solution (1.4 butanediol) | 4308 Resin-2 wt. % solution as diluted | Drain and stretch dry |
| 14 | 0.03 wt. % solution DGE(1.4 butanediol) | 1884 Resin-2 wt. % solution-pH as diluted | Drain and stretch dry |
| 15 | NONE | NONE-soak in water | Drain and stretch dry |

Parez 607-melamine formaldehyde cationic colloid
1884 Resin-Hercules 1884-polyamido-polyamine epichlorohydrin
Wesol PA-cationic colloidal silica
4308-Hercules Inc. R 4308 polyamido-polyamine epichlorohydrin resin.

TABLE XII(1 of 4)

SUMMARY OF TEST RESULTS

| SAMPLE NO. | THICKNESS (MILS) | | | IBP (PSI) | | | FAOP (PSI) | | | FLOW (ML/MIN) | | |
|---|---|---|---|---|---|---|---|---|---|---|---|---|
| | BT | AT | AE | BT | AT | AE | BT | AT | AE | BT | AT | AE |
| 1 | 4.67 | 4.52 | 4.70 | 45.00 | 45.25 | 44.70 | 49.25 | 48.50 | 49.00 | 86.25 | 90.70 | 87.0 |
| 2 | 4.75 | 4.75 | 4.80 | 44.62 | 43.62 | 44.50 | 49.87 | 48.00 | 48.80 | 87.25 | 76.50 | 94.0 |
| 3 | 4.77 | 4.67 | 4.70 | 43.50 | 45.75 | 44.50 | 49.87 | 50.12 | 48.30 | 85.00 | 84.00 | 94.0 |
| 4 | 4.57 | 4.85 | 4.85 | 43.75 | 45.75 | 46.00 | 49.75 | 50.50 | 50.25 | 81.75 | 2.62 | 86.00 |
| 5 | 4.67 | 4.70 | 4.70 | 44.62 | 44.37 | 43.50 | 48.75 | 49.12 | 50.25 | 88.25 | 93.25 | 83.00 |
| 6 | 4.70 | 4.90 | 4.80 | 44.87 | 46.37 | 45.0 | 49.25 | 51.75 | 50.72 | 87.50 | 49.00 | 85.00 |
| 7 | 4.80 | 4.70 | 4.85 | 43.87 | 46.37 | 44.25 | 48.87 | 50.62 | 49.50 | 86.25 | 83.25 | 91.00 |

BT - Before Treatment
AT - After Treatment
AE - After Extraction

TABLE XII (2 of 4)

SUMMARY OF TEST RESULTS

| SAMPLE | DYE ADSORPTION TIME TO B.T. (MIN) | | | ΔP CHARACTERISTIC* | | | EXTRACTION (MG/293 MM DISC) |
|---|---|---|---|---|---|---|---|
| | BT | AT | AE | BT | AT | AE | |
| 1 | 12.36 | 22.78 | 14.85 | $2.0_{2.2}$ | $2.0_{2.1}$ | $2.0_{2.0}$ | 27.6 |
| 2 | 12.39 | 34.67 | 23.86 | $2.0_{2.0}$ | $2.2_{2.2}$ | $2.0_{2.0}$ | 116.1 |
| 3 | 11.01 | 16.30 | 6.81 | $2.0_{2.0}$ | $2.0_{2.0}$ | $2.0_{2.0}$ | |
| 4 | 10.94 | — | 90.79 | $2.0_{2.0}$ | $>30$— | $2.1_{3.5}$ | 118.5 |
| 5 | 6.58 | 22.51 | 15.63 | $2.0_{2.0}$ | $1.8_{1.8}$ | $2.2_{2.2}$ | 24.3 |
| 6 | 5.96 | 37.54 | 21.06 | $2.0_{2.0}$ | $3.0_{2.3}$ | $2.2_{2.2}$ | 126.4 |
| 7 | 6.47 | 12.86 | 8.40 | $2.0_{2.0}$ | $2.3_{2.6}$ | $2.2_{2.2}$ | 43.9 |

BT - Before Treatment
AT - After Treatment
AE - After Extraction
B.T. - Breakthrough
*Upper Numbers are start of test and lower numbers are end of test.

TABLE XII(3 of 4)

SUMMARY OF TEST RESULTS

| SAMPLE NO. | THICKNESS (MILS) | | | IBP (PSI) | | | FAOP (PSI) | | | FLOW (ML/MIN) | | |
|---|---|---|---|---|---|---|---|---|---|---|---|---|
| | BT | AT | AE | BT | AT | AE | BT | AT | AE | BT | AT | AE |
| 8 | 4.82 | 4.80 | 4.90 | 44.12 | 46.75 | 43.5 | 49.12 | 51.75 | 49.25 | 88.75 | 1.30 | 91.50 |
| 9 | 4.67 | 4.85 | 4.90 | 45.37 | 45.25 | 46.00 | 49.37 | 49.75 | 50.00 | 86.75 | 87.50 | 81.00 |
| 10 | 4.77 | 4.77 | 4.85 | 45.12 | 44.12 | 45.25 | 49.62 | 49.87 | 49.50 | 87.25 | 91.25 | 87.50 |
| 11 | 4.75 | 4.90 | 5.00 | 45.87 | 44.37 | 47.50 | 50.75 | 49.75 | 51.00 | 83.50 | 29.00 | 83.50 |
| 12 | 4.87 | 4.77 | 4.90 | 44.00 | 46.12 | 46.00 | 49.62 | 49.87 | 49.50 | 84.25 | 70.00 | 85.00 |
| 13 | 4.77 | 4.85 | 4.90 | 44.12 | 45.00 | 46.70 | 49.50 | 48.75 | 50.00 | 85.00 | 45.00 | 89.50 |
| 14 | 4.80 | 4.90 | 5.00 | 44.62 | 46.37 | 44.50 | 50.25 | 50.37 | 49.00 | 85.00 | 73.50 | 92.00 |
| 15 | 4.82 | 4.72 | 4.95 | 44.75 | 45.06 | 46.50 | 48.87 | 49.62 | 50.00 | 86.25 | 85.50 | 84.00 |

BT - Before Treatment
AT - After Treatment
AE - After Extraction

TABLE XII (4 of 4)

SUMMARY OF TEST RESULTS

| SAMPLE | DYE ADSORPTION TIME TO B.T. (MIN) | | | ΔP CHARACTERISTIC* | | | EXTRACTION (MG/293 MM DISC) |
|---|---|---|---|---|---|---|---|
| | BT | AT | AE | BT | AT | AE | |
| 8 | 6.30 | — | 32.88 | $2.0_{2.0}$ | = | $2.1_{2.1}$ | 176.8 |
| 9 | 9.78 | 196.9 | 198.8 | $2.1_{2.1}$ | $2.1_{10.4}$ | $2.4_{24.5}$ | 85.2 |
| 10 | 7.86 | 79.60 | 73.39 | $2.1_{2.2}$ | $2.0_{2.1}$ | $2.2_{2.7}$ | 3.9 |
| 11 | 7.57 | 78.26 | 81.84 | $2.0_{2.0}$ | $6.5_{2.7}$ | $2.4_{5.7}$ | 68.4 |
| 12 | 7.24 | 28.60 | 11.99 | $2.0_{2.0}$ | $2.5_{2.2}$ | $2.1_{2.4}$ | 109.6 |
| 13 | 6.86 | 79.35 | 54.53 | $2.0_{2.0}$ | $2.9_{2.2}$ | $2.1_{2.7}$ | 54.0 |
| 14 | 7.34 | 22.03 | 14.95 | $2.0_{2.0}$ | $2.0_{2.2}$ | $2.2_{2.4}$ | 110.0 |
| 15 | 6.93 | 6.63 | 6.61 | $2.0_{2.0}$ | $2.0_{2.0}$ | $2.2_{2.4}$ | 9.0 |

BT - Before Treatment
AT - After Treatment
AE - After Extraction
B.T. - Breakthrough
*Upper Numbers are start of test and lower numbers are end of test.

SUMMARY

Samples 2, 4, 6, 8, 11, 12, 13 and 14, after treatment by the indicated mode exhibited a decrease in flow, i.e. the membranes exhibited clogged pores. This suggests that treatment with the polyamido-polyamine epichlorohydrin resins with a pH as diluted, i.e. less than 7, independent of pretreatment, exhibits pore clogging. After extraction (which tended to be high—less than 5 mg for 293 mm disc is acceptable for pharmaceutical uses) the flow rates increased indicating a reopening of the pores.

Dye adsorption tests indicated the retention of charge after extraction.

Samples 1 and 3, which were treated with trimethylol melamine formaldehyde cationic resin (see aforementioned U.S. Ser. No. 358,822 to Ostreicher) and cationic colloidal silica (see aforementioned U.S. Ser. No. 147,975 to Ostreicher et al) respectively, showed (a) marginal improvement in dye adsorption tests over untreated membrane, (b) intermediate levels of extraction and (c) even a decrease in dye adsorption after extraction (Sample 3). These tests indicate that the slight charge modification achieved was eliminated after extraction, i.e. the charge modifying agent was not bonded to the surface. Samples 5 and 7 indicate that charge modification, i.e. dye adsorption, after extraction is improved slightly after pretreatment with NaOH solution at pH 10.5, however, the charge modification is vastly inferior to the polyamido-polyamine epichlorohydrin charge modifying agents.

Samples 9 and 10 were both treated with polyamido-polyamine epichlorohydrin resin, Hercules R4308, adjusted to a pH of 10.5. Sample 10 was post-treated with tetraethylene pentamine. Both exhibited no clogging of pores after treatment. Sample 9 exhibited an unexpected enhancement of charge modification, which existed even after extraction over Sample 4 (or even 8) wherein the charge modifying agent was not pH adjusted. Sample 9, does however show an intermediate level of extraction. Sample 10 indicates the same unexpected enhancement of charge modification over Sample 4 (or even 8) but not as high. However, the extraction level is unexpectedly decreased to even below the untreated membrane (Sample 5) due to the post-treatment with the polyamine. Thus, preferred treatment mode for minimizing extraction levels is that of Sample 10. A preferred treatment mode for maximizing charge modification is that of Sample 9.

entrapment in the membrane which can prevent the charge modifying agent from diffusing into the membrane. The membrane was treated in this bath at a speed of 2.5 feet/min (76.2 cm/min) for a length of 4 feet (121.9 cm).

Upon exiting this bath, the membrane was wiped on the bottom surface to remove excess water. A 3 minute air soak with cool air movement was used before the membrane entered the secondary charge modifying agent bath.

This bath was produced by adding 0.023% tetraethylene pentamine by weight or 0.113 lbs. (0.0513 kg) to 60 gallons (227. liters) of D.I. water (at least 150,000 ohm-cm resistivity). The pH was about 9. The immersion conditions are identical to the first bath of primary charge modifying agent. The membrane was then wrapped around a take up roll.

The take up roll of wet membrane was stored for at least 3 hours. The roll was then dried at 250° F. (121° C.) for 3 minutes to complete the reaction of the charge modifying agents.

The membrane was then washed in a subsequent operation and checked for extraction levels.

EXAMPLE X

Membranes treated:
(1) Milliore Durapore GVHP (0.2 um, hydrophobic)
(2) Millipore Durapore GVWP (0.2 um, hydrophilic)

These membranes are microporous polyvinylidene difluoride, see Grandine II (U.S. Pat. Nos. 4,203,847 and 4,203,848).

Treatment Mode:
Contact with solutions:
Step 1: R4308, 2.0 wt.% solids in 20% (by volume) isopropyl/H2O
Step 2: Tetraethylene pentamine, 0.23 wt. % solids in 20% (by volume) isopropyl/H2O
Stretch dry at 75° C. for 20 minutes.

| Sample | IBP(PSI) | FAOP(PSI) | Q(ml/min) | Dye Adsorption - Time To Breakthru(Min) | Extraction (mg per 47 m m disc) |
|---|---|---|---|---|---|
| GVHP untreated | 3.0 | 5.0 | 0(at 15 PSID) | Not Run | 0.01 |
| GVHP treated | 4.0 | 15.0 | 0(at 15 PSID) | Not Run | 0.14 |
| GVWP untreated | 51.0 | 53.5 | 72.0 | 1 | 0.47 |
| GVWP treated | 50.0 | 54.0 | 75.0 | 56.0 | 0.18 |

Q - flow of water
Conclusion: Hydrophobic polymer membranes are not amenable to charge modification by the methods of this invention whereas hydrophilic versions of the same polymer are amenable to charge modification.

EXAMPLE IX

Best Mode

Two layers of wet microporous membrane, made as in Example IA, were laminated together and dried to 20–25% moisture. It has been found that membrane in such a wet, swollen condition absorbs charge modifying agents more efficiently than bone dry membrane.

The double layer of membrane was then introduced into a 1.25% by weight solution of Hercules R4308. The pH of the bath was 10.5.

This bath was produced by diluting 38 lbs. (17.17 Kg.) of Hercules R4308 resin from its initial 20% by weight concentration to 5%. Five normal (5N) sodium hydroxide solution was then added to raise the pH to 10.5. The solution was then diluted with D.I. water having greater than 150,000 ohm-cm resistivity in a ratio (volume) 2.5:1. The total volume of bath solution was 60 gallons.

The membrane entered the bath of Hercules R4308 at an angle of 30° from the horizontal to prevent bubble

EXAMPLE XI

Cellulose ester based microporous membranes:
(1) Millipore Type MF-HA-mixed cellulose acetate and nitrate, 0.45 micron rated;
(2) Sartorius Type SM-11306-cellulose nitrate, 0.45 micron rated; and
(3) Millipore Celotate -EH-cellulose acetate, 0.5 micron, were all treated with an aqueous siolution containing Hercules R4308 resin, 0.1 to 0.25% (by weight) tetraethylene pentamine and water (qs). The membranes were then dried at 80°–90° C. for 20—30 minutes. Tests (IBP, FAOP, flow tests and dye adsorption) indicate that significant charge modification had been achieved without deterioration in flow or bubble point characteristics.

What is claimed is:

1. A process for the filtration of particulates from a liquid comprising passing the liquid through a hydrophilic, cationic charge modified microporous filter membrane comprising:

a substantially isotropic, porous, hydrophilic, microporous cast nylon film membrane having a microstructure throughout said membrane; and a polyamido-polyamine epichlorohydrin cationic charge modifying agent having tertiary amine or quaternary ammonium groups, said agent being bonded to substantially all of said membrane microstructure without substantial pore size reduction or pore blockage, whereby the particulates are removed from the liquid by retention by the cationic charge modified membrane.

2. The process of claim 1, wherein the charge modifying agent is integral with the membrane.

3. A process for the filtration of particulates from a liquid comprising passing the liquid through a cationic charge modified microporous filter membrane comprising a substantially isotropic, hydrophilic, nylon membrane having micropores throughout the membrane, the surfaces of the micropores being modified by a charge modifying agent, said charge modifying agent being a polyamido-polyamine epichlorohydrin resin having tertiary amine or quaternary ammonium groups, whereby the particulates are removed from the liquid by retention by the cationic charge modified membrane.

4. The process of claim 3, wherein the charge modifying agent is integral with the membrane.

5. The process of claim 3, wherein the charge modifying agent is bonded to the nylon membrane.

6. The process of claim 1, 2, 3 or 4, wherein the charge modifying agent is the reaction product of epichlorohydrin with a polyamide.

7. The process of claim 1 or 2, wherein the charge modifying agent is the reaction product of diallylnitrogen-containing material with epichlorohydrin.

8. A process for the filtration of particulates from a liquid comprising passing the liquid through a cationic charge modified filter membrane comprising a substantially isotropic, hydrophilic, nylon film having micropores therethrough, the surfaces of the micropores being modified by a charge modifying agent, the agent being a resin which is the reaction product of diallylnitrogen-containing material with epichlorohydrin having tertiary amine or quaternary ammonium groups, whereby the particulates are removed from the liquid by retention by the cationic charge modified membrane.

9. The process of claim 8, wherein the charge modifying agent is integral with the nylon film.

10. The process of claim 1, 2, 3, 4, 5, 8 or 9, wherein the membrane further comprises a polyamine anchoring agent for the charge modifying agent which is tetraethylene pentamine.

11. The process of claim 1, 2, 3, 4, 5, 8 or 9, wherein the membrane further comprises a polyamine anchoring agent which is ethylene diamine or diethylene triamine.

* * * * *

UNITED STATES PATENT AND TRADEMARK OFFICE
CERTIFICATE OF CORRECTION

PATENT NO. : 4,708,803
DATED : November 24, 1987
INVENTOR(S) : Ostreicher et al.

It is certified that error appears in the above-identified patent and that said Letters Patent is hereby corrected as shown below:

In column 12, lines 26-30, please delete

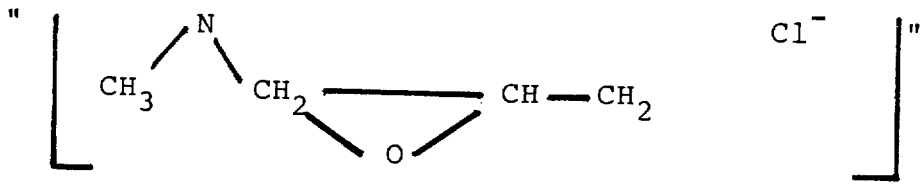

and substitute

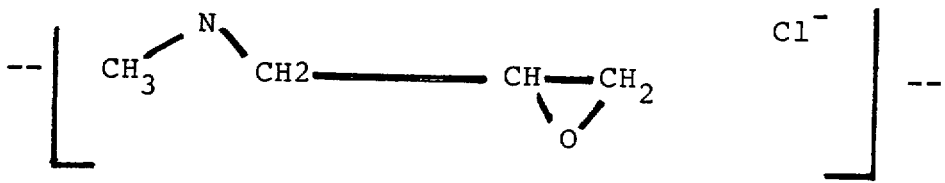

therefor.

Signed and Sealed this

Fourteenth Day of November, 1989

Attest:

JEFFREY M. SAMUELS

Attesting Officer    Acting Commissioner of Patents and Trademarks